(12) United States Patent
Knoblich et al.

(10) Patent No.: US 10,407,664 B2
(45) Date of Patent: Sep. 10, 2019

(54) THREE DIMENSIONAL HETEROGENEOUSLY DIFFERENTIATED TISSUE CULTURE

(71) Applicant: IMBA—Institut Fur Molekulare Biotechnologie GMBH, Vienna (AT)

(72) Inventors: Juergen Knoblich, Moedling (AT); Madeline A. Lancaster, Vienna (AT)

(73) Assignee: IMBA—Institut Fur Molekulare Biotechnologie GMBH, Vienna (AT)

( * ) Notice: Subject to any disclaimer, the term of this patent is extended or adjusted under 35 U.S.C. 154(b) by 201 days.

(21) Appl. No.: 14/651,346

(22) PCT Filed: Dec. 13, 2013

(86) PCT No.: PCT/EP2013/076552
§ 371 (c)(1),
(2) Date: Jun. 11, 2015

(87) PCT Pub. No.: WO2014/090993
PCT Pub. Date: Jun. 19, 2014

(65) Prior Publication Data
US 2015/0330970 A1  Nov. 19, 2015

(30) Foreign Application Priority Data
Dec. 13, 2012  (EP) ..................................... 12196954

(51) Int. Cl.
| | | |
|---|---|---|
| *C12N 5/0793* | (2010.01) | |
| *C12N 5/071* | (2010.01) | |
| *G01N 33/50* | (2006.01) | |
| *C12N 5/074* | (2010.01) | |

(52) U.S. Cl.
CPC ......... *C12N 5/0619* (2013.01); *C12N 5/0696* (2013.01); *C12N 5/0697* (2013.01); *G01N 33/5058* (2013.01); *C12N 2501/33* (2013.01); *C12N 2501/91* (2013.01); *C12N 2506/02* (2013.01); *C12N 2506/45* (2013.01); *C12N 2513/00* (2013.01); *C12N 2533/90* (2013.01)

(58) Field of Classification Search
CPC .................................................... C12N 5/0619
See application file for complete search history.

(56) References Cited

U.S. PATENT DOCUMENTS

| | | | |
|---|---|---|---|
| 2007/0178586 A1 | 8/2007 | Yang et al. | |
| 2011/0091869 A1* | 4/2011 | Sasai ................... | C12N 5/0623 435/5 |
| 2013/0149287 A1* | 6/2013 | Livesey ............... | C12N 5/0619 424/93.7 |

FOREIGN PATENT DOCUMENTS

| | | |
|---|---|---|
| EP | 2314671 A1 | 4/2011 |
| WO | 2004/053096 A2 | 6/2004 |
| WO | 2011/055855 A1 | 5/2011 |
| WO | 2012/013936 A1 | 2/2012 |

OTHER PUBLICATIONS

Molnar et al, "Hanging by the tail: progenitor populations proliferate" Nature Neuroscience, 2011, vol. 14, No. 5, pp. 538-540.*
Fietz et al, PNAS, 2012, vol. 109, No. 29, pp. 11836-11841.*
Lancester et al, Nature, 2013, vol. 501, pp. 373-379.*
Kadoshima et al, "Self-organization of axial polarity, inside-out layer pattern, and species-specific progenitor dynamics in human ES cell-derived neocortex" PNAS, 2013, vol. 110, No. 50, pp. 20284-20289. (Year: 2013).*
European Search Report for Application No. EP12196954.7, dated Sep. 2, 2013 (5 pages).
International Search Report of the International Searching Authority for Application No. PCT/EP2013/076552, dated Jun. 19, 2014 (5 pages).
Written Opinion of the International Searching Authority for Application No. PCT/EP2013/076552 (4 pages).
First Written Opinion of the International Preliminary Examining Authority for Application No. PCT/EP2013/076552, dated Nov. 11, 2014 (4 pages).
Second Written Opinion of the International Preliminary Examining Authority for Application No. PCT/EP2013/076552, dated Dec. 23, 2014 (4 pages).
International Preliminary Report on Patentability of the International Preliminary Examining Authority for Application No. PCT/EP2013/076552, dated Mar. 12, 2015 (7 pages).
Oliver Brustle, "Developmental Neuroscience: Miniature Human Brains" Nature, vol. 501, Sep. 19, 2013: pp. 319-320.
Chambers et al., "Build-a-Brain". Cell Stem Cell, vol. 13, Oct. 3, 2013: pp. 377-378.
Wang et al., "A new subtype of progenitor cell in the mouse embryonic neocortex". Nat Neurosci., vol. 14, No. 5, May 2011: pp. 555-561.
Barrera et al., "CDK5RAP2 Regulates Centriole Engagement and Cohesion in Mice". Dev Cell, vol. 18, No. 6, Jun. 15, 2010: pp. 913-926.
Bond et al., "ASPM is a major determinant of cerebral cortical size". Nature Genetics, vol. 32, Oct. 2002: pp. 316-320.
Bond et al., "A centrosomal mechanism involving CDK5RAP2 and CENPJ controls brain size". Nature Genetics, vol. 37, No. 4, Apr. 2005: pp. 353-355.
Cox et al., "What primary microcephaly can tell us about brain growth". Trends in Mol Med, vol. 12, No. 8, 2006: pp. 358-366.
Eiraku et al., "Self-Organized Formation of Polarized Cortical Tissues from ESCs and Its Active Manipulation by Extrinsic Signals". Cell Stem Cell, vol. 3, Nov. 6, 2008: pp. 519-532.

(Continued)

*Primary Examiner* — Allison M Fox
(74) *Attorney, Agent, or Firm* — Nutter McClennen & Fish LLP

(57) ABSTRACT

The present invention provides an artificial tissue culture comprising a heterogeneous population of cells of at least two different tissue sections, wherein said tissue sections are in a three dimensional structure, method of generating such a tissue and kits suitable for said method or maintain a three dimensional tissue culture.

Figure 1:
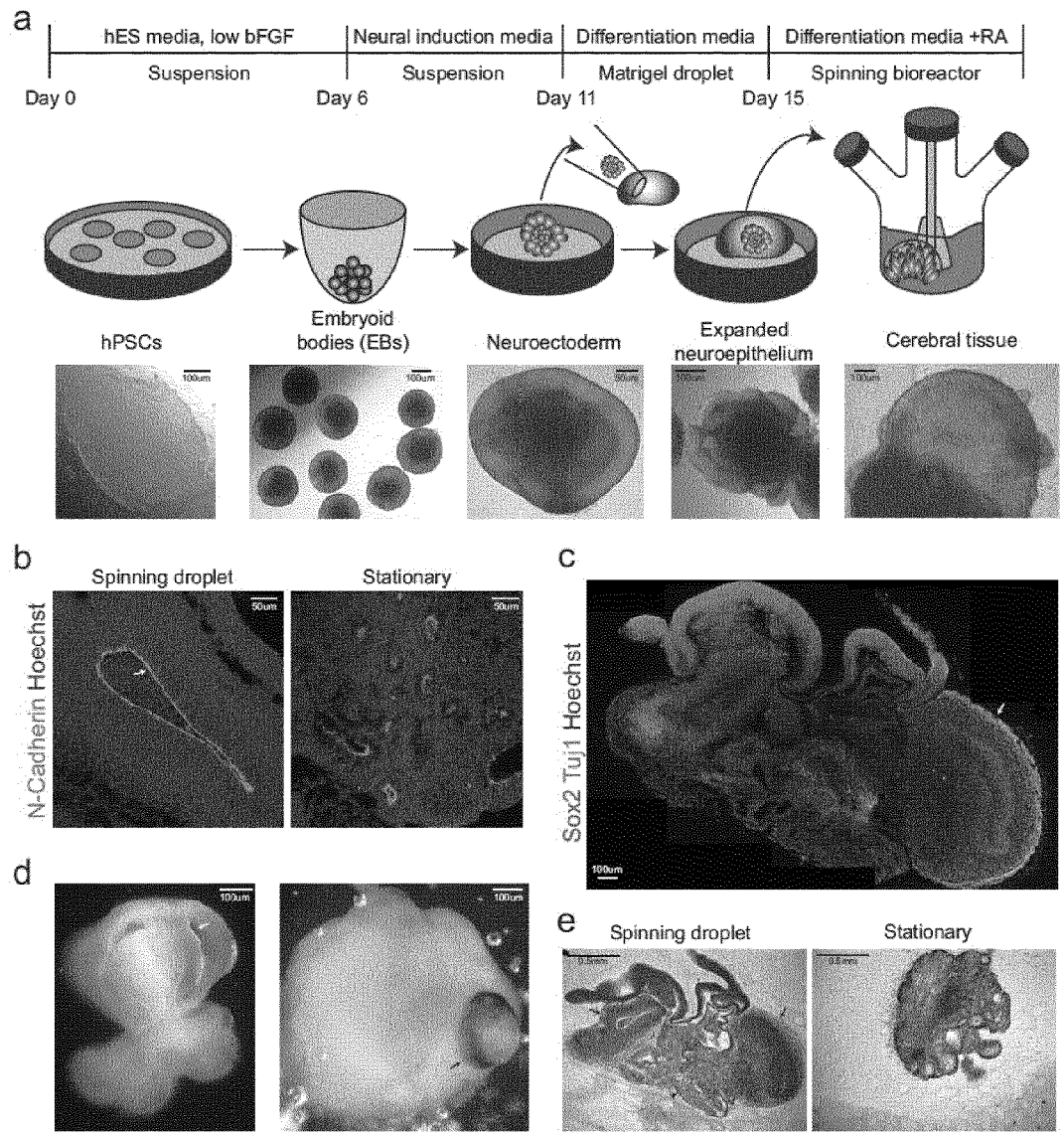

18 Claims, 21 Drawing Sheets
Specification includes a Sequence Listing.

(56) References Cited

OTHER PUBLICATIONS

Elkabetz et al., "Human ES cell-derived neural rosettes reveal a functionally distinct early neural stem cell stage". Genes & Dev, vol. 22, 2008: pp. 152-165.
Simone A Fietz and Wieland B Huttner, "Cortical progenitor expansion, self-renewal and neurogenesis—a polarized perspective". Curr Op in Neurobiol, vol. 21, 2011: pp. 23-35.
Fietz et al., "OSVZ progenitors of human and ferret neocortex are epithelial-like and expand by integrin signaling". Nature Neuroscience, vol. 13, No. 6, Jun. 2010: pp. 690-699.
Magdalena Gotz and Wieland B. Huttner, "The Cell Biology of Neurogenesis". Mol Cell Biol, vol. 6, Oct. 2005: pp. 777-788.
Hansen et al., "Neurogenic radial glia in the outer subventricular zone of human neocortex". Nature, vol. 464, Mar. 25, 2010: pp. 554-561.
Kenny et al., "The morphologies of breast cancer cell lines in three-dimensional assays correlate with their profiles of gene expression". Molecular Oncology, vol. 1, 2007: pp. 84-96.
Koch et al., "A rosette-type, self-renewing human ES cell-derived neural stem cell with potential for in vitro instruction and synaptic integration". PNAS, vol. 106, No. 9, Mar. 3, 2009: pp. 3225-3230.
Lizarraga et al., "Cdk5rap2 regulates centrosome function and chromosome segregation in neuronal progenitors". Development, vol. 137, No. 11, Jun. 2010: pp. 1907-1917.
Lui et al., "Development and Evolution of the Human Neocortex". Cell, vol. 146, No. 1, Jul. 8, 2011: pp. 18-36.
Megraw et al., "Cdk5rap2 Exposes the Centrosomal Root of Microcephaly Syndromes". Trends Cell Biol, vol. 21, No. 8, Aug. 2011: pp. 470-480.
Paul J. Price and Gregory J. Brewer, "Chapter Nineteen: Serum-Free Media for Neural Cell Cultures: Adult and Embryonic". Protocols for Neural Cell Culture, 3rd Ed., 2001: pp. 255-264.
Pulvers et al., "Mutations in mouse Aspm (abnormal spindle-like microcephaly associated) cause not only microcephaly but also major defects in the germline". PNAS, vol. 107, No. 38, Sep. 21, 2010: pp. 16595-16600.
Brent A. Reynolds and Samuel Weiss, "Generation of Neurons and Astrocytes from Isolated Cells of the Adult Mammalian Central Nervous System". Science, vol. 255, Mar. 27, 1992: pp. 1707-1710.
Sato et al., "Single Lgr5 stem cells build crypt-villus structures in vitro without a mesenchymal niche". Nature, vol. 459, May 14, 2009: pp. 262-265.
Shi et al., "Human cerebral cortex development from pluripotent stem cells to functional excitatory synapses". Nat Neurosci, vol. 15, No. 3, Feb. 5, 2012: pp. 477-486.
Gemma K. Thornton and C. Geoffrey Woods, "Primary microcephaly: do all roads lead to Rome?". Trends in Genetics, vol. 25, No. 11, Nov. 2009: pp. 501-510.
Tremml et al., "Culture of Mouse Embryonic Stem Cells". Current Protocols in Stem Cell Biology, 2008: pp. 1C.4.1-1C.4.19.
Patricia G. Wilson and Steve S. Stice, "Development and Differentiation of Neural Rosettes Derived From Human Embryonic Stem Cells". Stem Cell Reviews, vol. 2, No. 1, 2006: pp. 67-77.
Xiaofeng Xia and Su-Chun Zhang, "Differentiation of neuroepithelia from human embryonic stem cells". Methods Mol Biol, vol. 549, 2009: pp. 51-58.
Zhang et al., "In vitro differentiation of transplantable neural precursors from human embryonic stem cells". Nature Biotechnology, vol. 19, Dec. 2001: pp. 1129-1133.
European Office Action dated Oct. 28, 2016, for Application No. 13803067.1 (6 pages).
Novak, U., et al., "Extracellular matrix and the brain: components and function," J. Clin. Neuroscience, 2000, v. 7, pp. 280-290.

\* cited by examiner

Figure 7
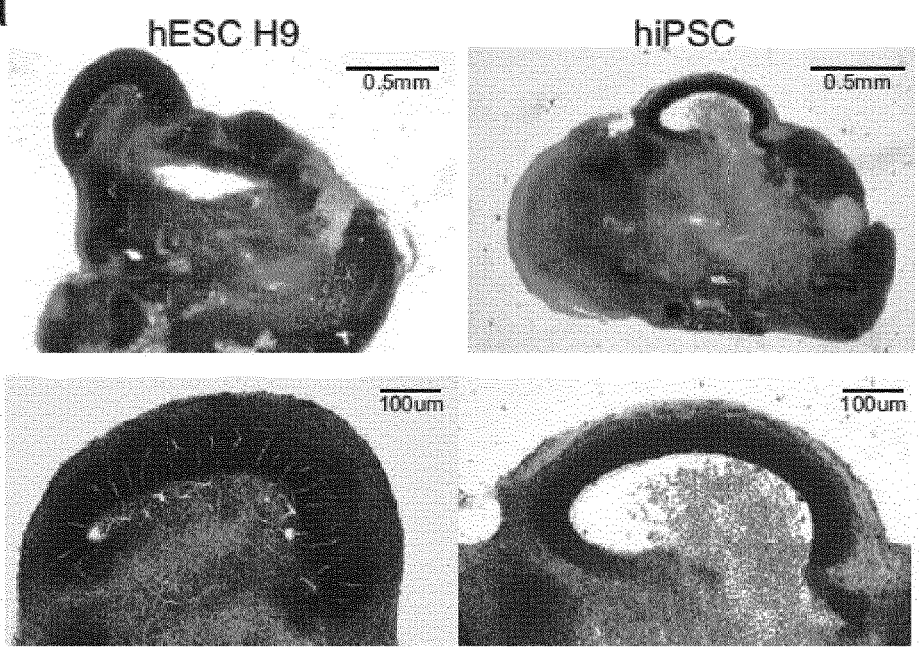
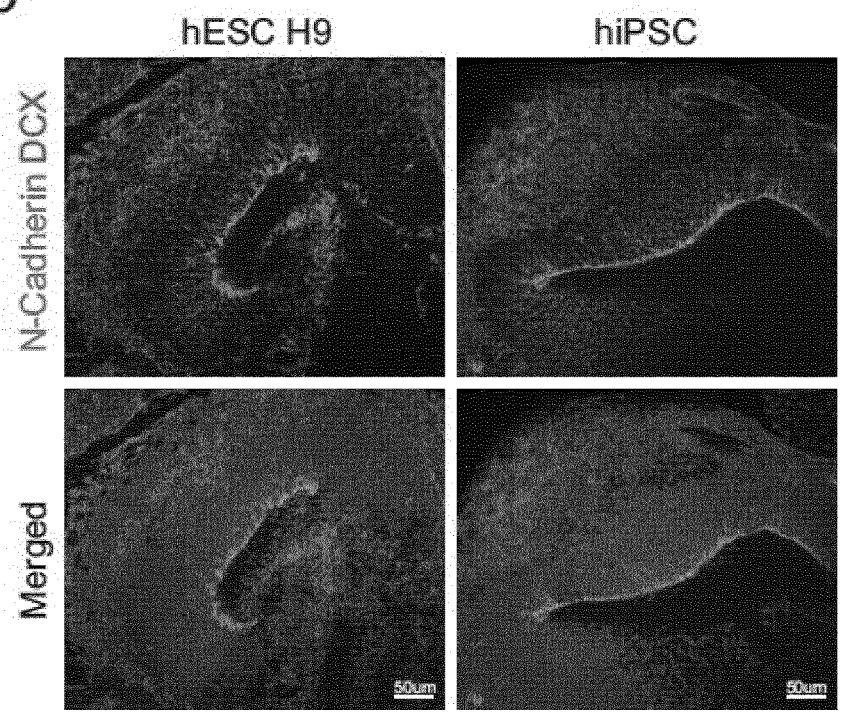

Figure 11
a
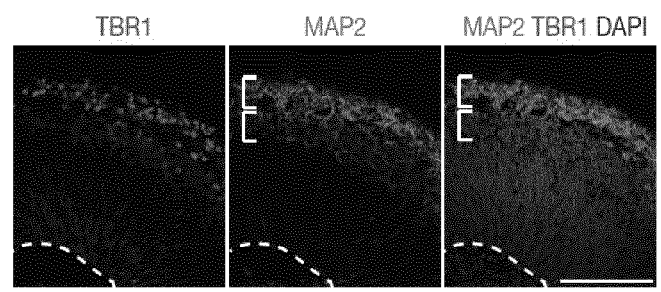
b
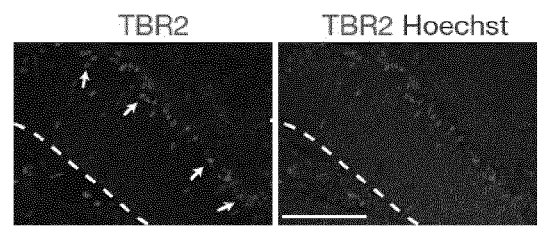

Figure 17
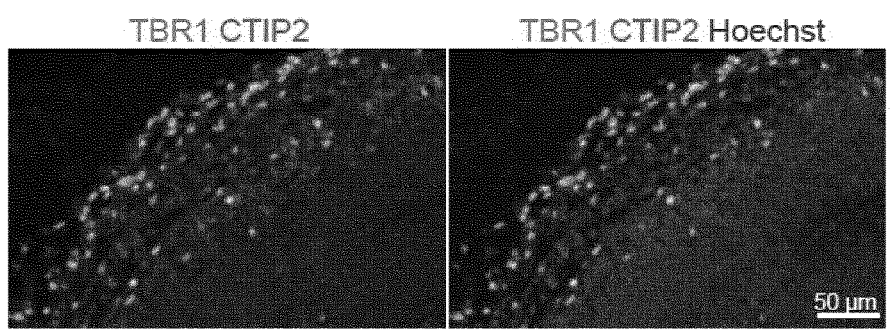
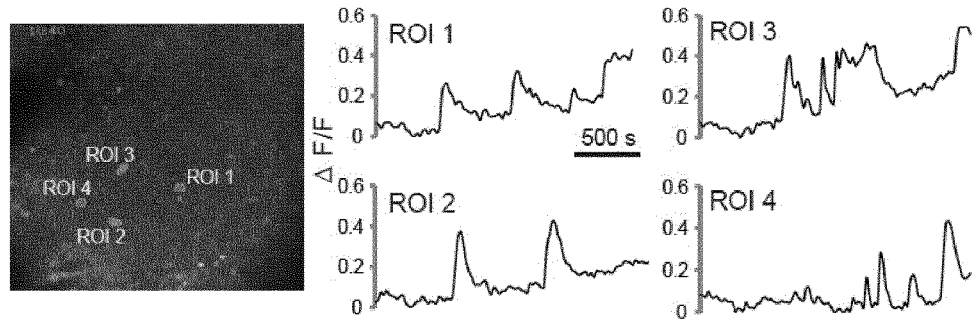

THREE DIMENSIONAL HETEROGENEOUSLY DIFFERENTIATED TISSUE CULTURE

The present invention relates to the field of modelling artificial tissue cultures.

Development of the human brain is of primary interest in neuroscience, both due to the nature of its complexity and because defects in development of this unique organ can lead to a variety of devastating neurological disorders. For example, microcephaly (MCPH), a disorder marked by a severely reduced head and brain size, leads to neurological defects with a poor prognosis for normal brain function (Cox et al. 2006).

Several genes have been identified as causative for MCPH (Thornton and Woods. 2009), for example ASPM (Bond et al. 2002) and CDK5RAP2 (Bond et al. 2005), and there is evidence for all of them so far pointing to a role at the centrosome or spindle pole of dividing cells (Megraw et al. 2011). In particular, ASPM is the human homolog of the *drosophila* abnormal spindle (asp) while CDK5RAP2 is the homolog of centrosomin (cnn), both of which regulate centrosomal and spindle organization.

Heretofore, efforts aimed at teasing out pathogenic mechanisms of MCPH and the roles of these proteins in human brain development have relied upon mouse models. However, mouse mutants for these genes, including CDK5RAP2 (Barrera et al. 2010, Lizarraga et al. 2010) and ASPM (Pulvers et al. 2010), have failed to recapitulate the severely reduced brain size seen in human patients with mutations in these genes.

Much of the current knowledge of mammalian brain development has come from rodent studies, which have revealed many of the fundamental mechanisms of mammalian neurogenesis. In rodents as well as humans, brain development begins with expansion of the neuroepithelium to generate a type of neural progenitor termed radial glia (RG) (Götz and Huttner. 2005). These RGs divide at the apical surface within the ventricular zone (VZ) either symmetrically to generate two more RGs or asymmetrically to generate a RG and a more differentiated daughter cell, a neuron or intermediate progenitor. These then migrate outward into the subventricular zone (SVZ) while the neurons continue migrating through the intermediate zone (IZ) to populate specified layers within the cortical plate (CP).

Although the human brain follows these same basic principles during early development, there are several key differences from rodents that allow for the striking expansion in neuronal output seen in humans as development proceeds (Fietz and Huttner. 2011, Lui et al. 2011). For example, the human brain exhibits a large population of a novel stem cell termed outer radial glia (oRG) (Fietz et al. 2010, Hansen et al. 2010), which can divide symmetrically and asymmetrically, much like the radial glia in the VZ, to expand the neuronal output. This population is only present to a very limited degree in rodents, whereas in humans they make up an entirely separate progenitor layer, termed the outer SVZ (OSVZ). Furthermore, the organization of progenitor zones is markedly more elaborate in humans, exhibiting a SVZ that is split by an inner fiber layer (IFL) into an inner SVZ (ISVZ) and the OSVZ. Both the IFL and OSVZ are completely absent in mouse.

These differences can explain the difficulties in modeling disorders like MCPH in rodents, and suggest that these disorders may originate from defects in neurodevelopmental processes that cannot be examined in mice. Therefore, methods that recapitulate paradigms of human brain development in vitro have enormous potential.

A variety of culture systems have been described for the derivation of human neurons from pluripotent stem cells. Most of these approaches make use of so-called neural rosettes (Wilson and Stice. 2006), which display characteristics of neuroepithelium and can be used to drive the formation of pure populations of specific neuronal subtypes. However, these approaches are limited in their capacity to model many aspects of human brain development as they fail to recapitulate the complexity and heterogeneity seen in vivo.

WO 2011/055855 A1 discloses differentiation of human embryonic stem cells into nerve progenitor cells and cup-like protrusion tissue.

WO 2012/013936 A1 discloses differentiation of neuronal cells and cultures. Stem and progenitor cells are disclosed which form rosette structures.

EP 2 314 671 A1 discloses cultures derived from human embryonic stem cells.

Wang et al. (2011) describe the identification of radial glia-like progenitor cells in mice.

While significant progress has been made in developing in vitro models of whole organ development for other systems, such as mammary gland (Kenny et al. 2007), intestine (Sato et al. 2009), and retina (Eiraku et al. 2011, WO 2011/055855 A1), a 3D culture model of the developing brain as a whole has not been established. However, previous studies have pointed to a principle of self-organization for several isolated neural tissues suggesting an approach may be possible. In particular, Eiraku et al. (2008), US 2011/0091869 A1, have described the formation of dorsal cerebral cortical tissue in three-dimensional culture from pluripotent stem cells. This study reveals the remarkable ability for cerebral cortical tissue to self-organize, and these tissues recapitulated many aspects of early dorsal cortical development. However, the tissues generated were limited in their identity to dorsal cortex of the forebrain, and while the neurons generated displayed pyramidal subtype identities and activity, they failed to form discrete layers with stereotypic inside-out organization. Furthermore, characteristics of human brain development, such as the presence of outer radial glial cells and the unique organization of progenitor zones were not present.

It is therefore a goal of the present invention to provide new tissue models based on cell cultures, which represent in vivo tissue behavior.

The present invention relates to an artificial three-dimensional neuronal tissue culture comprising a heterogenous population of cells of at least two different progenitor and neuronal differentiation layers, wherein at least one progenitor layer comprises outer radial glia cells. The new neuronal tissue is also referred to as "organoid" or "cerebral organoids" herein. The cerebral organoids display heterogeneous regionalization of various brain regions as well as development of complex, well-organized cerebral cortex. Furthermore, these tissues display several characteristics specific to humans, namely the presence of a substantial outer radial glial population and the organization of extra cortical subventricular zone layers not present in mouse. The presence of outer radial glia cells appears to be one of the most distinguishing features, but of course others exist as well. Eiraku et al. (2008) for example describes that in their culture radial glia of cortical tissues decreased after day 12 and apparently failed to develop into outer radial glia cells, outer radial glia being characterized by their position as well as morphology (lack of an apical connection to the fluid-filled ventricular-like cavity). According to the invention, the outer radial glia cells are preferably in a progenitor layer, in particular, in a subventricular zone removed from the ventricular zone where radial glia reside. Other alternative distinguishing features are further described below, e.g. the genetic expression markers.

The invention further provides a method of generating an artificial three-dimensional neuronal tissue culture comprising a multicellular aggregation of pluripotent stem cells, culturing said multicellular aggregation in neural induction medium, further culturing in a three dimensional matrix, preferably a gel, thereby expanding said cells in a multicellular aggregation, wherein said cells are allowed to differentiate, and culturing said expanded and optionally differentiated multicellular aggregation of cells in a suspension culture. Various progenitor and neuron populations could be produced, which display proper organization and behaviour.

Methods for culturing and differentiating stem cells into neuronal cells and tissues are known from Eiraku (2008), US 2011/0091869 A1 and WO 2011/055855 A1, all incorporated by reference. Methods described therein can be used in the first step of obtaining the inventive tissue, especially the steps of providing a multicellular aggregation of pluripotent stem cells and culturing said multicellular aggregation in neural induction medium. During the step of culturing the aggregate, the pluripotent stem cells can be induced to differentiate to neural tissue. For providing a multicellular aggregation, it is e.g. possible to culture pluripotent stem cells from said multicellular aggregates. Contrary to these references, the invention further comprises the step of culturing the cell aggregates in a three dimensional matrix, preferably a gel, which surprisingly resulted in far more advanced tissue development.

The invention particularly relates to a new method for generating large, complex brain tissues using a 3D in vitro culture system. Individual tissue-like sections of different differentiated cells of the inventive culture can be in a three dimensionally grown arrangement. The resulting cerebral organoids develop a variety of regional identities organized as discrete domains capable of influencing one another, much like the brain as a whole. Furthermore, cerebral cortical regions display an organization similar to the developing human brain as well as the presence of a considerable oRG population. Moreover, cerebral cortical neurons mature to form various pyramidal identities and even organize in an inside-out manner reminiscent of cortical layers in vivo. The organoid can be used to model neurological diseases, e.g. MCPH. In particular, the invention demonstrates utilizing patient-derived iPSCs and shRNA electroporations in these organoids to model pathogenesis of MCPH, a disorder that has been difficult to model in mice.

The inventive organoids can be obtained from culturing pluripotent stem cells. In principle, the cells may also be totipotent, if ethical reasons allow.

A "totipotent" cell can differentiate into any cell type in the body, including the germ line following exposure to stimuli like that normally occurring in development. Accordingly, a totipotent cell may be defined as a cell being capable of growing, i.e. developing, into an entire organism.

The cells used in the methods according to the present invention are preferably not totipotent, but (strictly) pluripotent.

In a particular preferred embodiment, the cells of the present invention (including all further embodiments related thereto), are human cells or non-human primate cells, pluripotent.

A "pluripotent" stem cell is not able of growing into an entire organism, but is capable of giving rise to cell types originating from all three germ layers, i.e., mesoderm, endoderm, and ectoderm, and may be capable of giving rise to all cell types of an organism. Pluripotency can be a feature of the cell per see, e.g. in certain stem cells, or it can be induced artificially. E.g. in a preferred embodiment of the invention, the pluripotent stem cell is derived from a somatic, multipotent, unipotent or progenitor cell, wherein pluripotency is induced. Such a cell is referred to as induced pluripotent stem cell herein. The somatic, multipotent, unipotent or progenitor cell can e.g. be used from a patient, which is turned into a pluripotent cell, that is subject to the inventive methods. Such a cell or the resulting tissue culture can be studied for abnormalities, e.g. during tissue culture development according to the inventive methods. A patient may e.g. suffer from a neurological disorder or cerebral tissue deformity. Characteristics of said disorder or deformity can be reproduced in the inventive organoids and investigated.

A "multipotent" cell is capable of giving rise to at least one cell type from each of two or more different organs or tissues of an organism, wherein the said cell types may originate from the same or from different germ layers, but is not capable of giving rise to all cell types of an organism.

In contrast, a "unipotent" cell is capable of differentiating to cells of only one cell lineage.

A "progenitor cell" is a cell that, like a stem cell, has the ability to differentiate into a specific type of cell, with limited options to differentiate, with usually only one target cell. A progenitor cell is usually a unipotent cell, it may also be a multipotent cell.

With decreasing differentiation capabilities, stem cells differentiate in the following order: totipotent, pluripotent, multipotent, unipotent. During development of the inventive organoid, stem cells differentiate from pluripotent (also totipotent cells are possible) into multipotent neural stem cells, further into unipotent stem cells of a cerebral layer and subsequently into non-stem tissue cells. Tissue cells may e.g. be neuronal cells or neuroepithelial cells, such as glial cells.

The inventive tissue culture is in vitro grown, i.e. it is not an isolated brain from an animal during any stages. Since it is grown from human pluripotent stem cells, this allows growth of human brain tissue without the need to obtain human fetal brain tissue samples. In addition, this system represents growth of derived brain tissue in 3D, whereas isolated animal brain tissues have only been used in 3D to generate neurospheres, an aggregation of dissociated neural stem cells with limited multipotent capacity (Reynolds and Weiss. 1992). These neurospheres fail to recapitulate many aspects of in vivo brain development e.g. regional identities, progenitor and differentiation layer organization, neuronal layering organization, which can be provided by the inventive tissue culture and/or methods. The inventive tissue culture is not and differs according to these aspects from a neurosphere.

During the development, the cell aggregates form polarized neuroepithelial structures and a neuroepithelial sheet, which will develop several round clusters (rosettes). These steps can be controlled by neural induction medium as described by Eiraku (2008), US 2011/0091869 A1 and WO 2011/055855 A1. In the absence of neural induction medium, e.g. by using standard differentiation media, the invention further comprises culturing in a three dimensional matrix, preferably a gel, especially a rigid stable gel, which results in further expansion of neuroepithelium and differentiation. A suitable three dimensional matrix may comprise collagen. More preferably the three dimensional matrix comprises extracellular matrix from the Engelbreth-Holm-Swarm tumor or any component thereof such as laminin, collagen, preferably type 4 collagen, entactin, and optionally further heparan-sulfated proteoglycan or any combination thereof. Such a matrix is Matrigel. Matrigel is known in the art (U.S. Pat. No. 4,829,000) and has been used to model 3D heart tissue previously (WO 01/55297 A2). Preferably the matrix comprises a concentration of at least 3.7 mg/ml containing in parts by weight about 60-85% laminin, 5-30% collagen IV, optionally 1-10% nidogen, optionally 1-10% heparan sulfate proteoglycan and 1-10% entactin. Matrigel's solid components usually comprise approximately 60% laminin, 30% collagen IV, and 8% entactin. Entactin is a bridging molecule that interacts with laminin and collagen. The three dimensional matrix may further comprise growth factors, such as any one of EGF (epidermal growth factor), FGF (fibroblast growth factor), NGF, PDGF, IGF (insulin-like growth factor), especially IGF-1, TGF-β, tissue plasminogen activator. The three dimensional matrix may also be free of any of these growth factors.

In general, the three dimensional matrix is a three dimensional structure of a biocompatible matrix. It preferably comprises collagen, gelatin, chitosan, hyaluronan, methylcellulose, laminin and/or alginate. The matrix may be a gel, in particular a hydrogel. Organo-chemical hydrogels may comprise polyvinyl alcohol, sodium polyacrylate, acrylate polymers and copolymers with an abundance of hydrophilic groups. Hydrogels comprise a network of polymer chains that are hydrophilic, sometimes found as a colloidal gel in which water is the dispersion medium. Hydrogels are highly absorbent (they can contain over 99% water) natural or synthetic polymers. Hydrogels also possess a degree of flexibility very similar to natural tissue, due to their significant water content.

After the expansion, the cell aggregates can be cultured in suspension culture, preferably a bioreactor. Said culturing in suspension culture is preferably also in the absence of neural induction medium. A suitable medium is a standard differentiation medium.

In preferred embodiment the medium can comprise or lack the following components:

Medium A for the step of culturing pluripotent stem cells as an aggregate (termed an embryoid body): serum replacement formulation, fetal bovine serum, glutamine, non-essential amino acids, 2-mercaptoethanol, bFGF, preferably about 4 ng/ml bFGF, or any combination thereof. Especially preferred, this medium contains a ROCK inhibitor for the initial stages of aggregate culture. Such a medium is e.g. hES medium used in the examples.

Medium B the step of differentiating the aggregate of pluripotent stem cells to neural tissue: N2 supplement (Price and Brewer. 2001), glutamine, non-essential amino acids, heparin, or any combination thereof. This medium preferably lacks growth factors that would differentiate neural tissue to a particular fate. Such absent growth factors may be any one of Shh, Wnt, Bmp, retinoids, or FGF, or any combination thereof, especially all of them. Such a medium is e.g. neural induction medium used in the examples.

Medium C for the step of culturing in a three dimensional matrix, preferably a gel: N2 supplement (Price and Brewer. 2001), B27 supplement (Price and Brewer. 2001), insulin, 2-mercaptoethanol, glutamine, non-essential amino acids, or any combination thereof. This medium preferably lacks growth factors that would differentiate neural tissue to a particular fate. Such absent growth factors may be any one of Shh, Wnt, Bmp, retinoids, or FGF, or any combination thereof, especially all of them. Such a medium is e.g. differentiation medium used in the examples.

Medium D for the step of culturing in a suspension culture, preferably a bioreactor: N2 supplement, B27 supplement, insulin, 2-mercaptoethanol, glutamine, non-essential amino acids, or any combination thereof. This medium preferably lacks growth factors that would differentiate neural tissue to a particular fate. Such absent growth factors may be any one of Shh, Wnt, Bmp, or FGF, or any combination thereof, especially all of them. Preferably this medium contains retinoic acid to promote pyramidal differentiation and maturation. Such a medium is e.g. "differentiation medium+RA" used in the examples.

Any medium further contains nutrients, buffers, oxygen. The medium may further comprise growth factors or lack growth factors. Growth factors which may be present or missing are e.g. EGF, FGF, NGF, PDGF, IGF, especially IGF-1, TGF-β, tissue plasminogen activator. Preferred nutrients include a carbohydrate, especially a mono-hexose or mono-pentose, such as glucose or fructose. In preferred embodiments any one of the media, preferably all, are serum-free.

The step of culturing pluripotent stem cells is preferably performed for a duration of 2 to 8 days, especially preferred 5 to 7 days. In particular, said step may be performed on culture days 0 to 8. The step of culturing the aggregate of pluripotent stem cells is preferably performed for a duration of 2 to 7 days, especially preferred 4 to 6 days. In particular, said step may be performed on culture days 5 to 14. The step of culturing in a three dimensional matrix, preferably a gel is preferably performed for a duration of 1 to 6 days, especially preferred 3 to 5 days. In particular, said step may be performed on culture days 9 to 18. The following step of culturing in a suspension culture is preferably performed for a duration of at least 3 days, especially preferred at least at least 4 or at least 5 days.

In preferred embodiments the suspension culture (especially the suspension culture after culturing in a 3D matrix) is a stirring or shaking medium culture, in particular preferred a bioreactor. At this stage, the inventive culture has reached enlarged size dependent on constant nutrient supply. This is best achieved by flushing of the cells, e.g. by stirring or shaking.

In preferred embodiment, during cell expansion, especially in the 3D matrix the cells are allowed to differentiate into unipotent stem cells (progenitor cells). During this step tissue-like development proceeds comprising the formation of distinctive layers, including layers of unipotent cells occurs, which give rise to specialized nerve or epithelial cells.

The present invention also relates to a cell or tissue culture obtainable by said methods. In particular, the invention provides an in vitro grown artificial three-dimensional neuronal tissue culture ("organoid") comprising a heterogeneous population of cells of at least two different neuronal differentiation layers. As mentioned above, preferably at least one differentiation layer comprises outer radial glia cell.

The inventive culture may develop into a differentiated tissue comprising layers of different differentiation grade. In a 3D structure this may be observable as separate sections of the cultures. In preferred embodiments, the culture comprises tissue sections form at least two layers. Such a layer may be shaped around a globular tissue body, e.g. a body from which the distinct layer(s) have developed. In particular, the tissue may show a distinctive development of apical and dorsal tissue sections.

The inventive tissue is or resembles cerebral tissue comprising substantially all cells found in the brain or progenitors thereof. Such cells can be identified by selective gene expression markers, which are on a level above the average of not differentiated cells, in particular including confidence intervals. Such markers can be identified by specific oligonucleotide probes, which preferably bind exclusively to said target marker nucleic acid, especially target marker mRNA. Markers can further be identified by specific antibodies.

Preferably cells of the inventive culture express one or more gene expression markers selected from forebrain markers BF1 and Six3. Alternatively, or in addition, preferably cells of the inventive culture express one or more gene expression markers selected from hindbrain markers Krox20 and Ils1. At a certain stage of development forebrain markers are expressed in increased amounts as compared to hindbrain markers in the tissue. This is preferably reflected in the culture of the invention.

The inventive tissue culture can alternatively or in addition be characterized by comprising cells expressing one or more gene expression markers selected from Otx1, Otx2, FoxG1, Auts2, Tbr2, Tuj1, Brn2, Satb2, Ctip2, calretinin, or any combination thereof. These markers may be expressed during any stage of the culture during the inventive method, and are preferably expressed in the provided tissue culture.

Preferably the inventive culture comprises cells, which express Otx1 and/or Oxt2. Otx1 and/or Oxt2 are expressed in cells of forebrain/midbrain identity. Preferably this tissue type is comprised in the inventive culture.

Preferably the inventive culture comprises cells, which express FoxG1. FoxG1 is expressed in cells of dorsal cortex identity. Preferably this tissue type is comprised in the inventive culture.

Preferably the inventive culture comprises cells, which express Auts2. Auts2 is expressed in cells of frontal cortex identity. Preferably this tissue type is comprised in the inventive culture.

Preferably the inventive culture comprises cells, which express Tuj1. Tuj1 is expressed in cells of a cortical inner fiber layer identity. Preferably this tissue type is comprised in the inventive culture. Generation of an inner fiber layer (and also an outer subventricular zone) have never been achieved before and are indicators of the inventive tissue.

Preferably the inventive culture comprises cells, which express Brn2. Brn2 is expressed in cells of a later born neuron (neuron of outer region). Preferably this tissue type is comprised in the inventive culture.

Preferably the inventive culture comprises cells, which express Satb2. Satb2 is expressed in cells of a later born neuron (neuron of outer region). Preferably this tissue type is comprised in the inventive culture.

Preferably the inventive culture comprises cells, which express Ctip2. Ctip2 is expressed in cells of earlier born neuron (neuron of inner region). Preferably this tissue type is comprised in the inventive culture.

Preferably the inventive culture comprises cells, which express calretinin. Calretinin is expressed in cells of cortical interneurons within the dorsal cortical plate. Preferably this tissue type and/or the cortical interneurons is/are comprised in the inventive culture.

The inventive artificial tissue can also be used as a research tool to study the effects of any external (e.g. drugs or other stimuli) or internal (mutations) influences on growth and activity of cells in the tissue. Therefore, in an additional aspect, the invention provides a method of investigating a developmental neurological tissue effect, e.g. a defect, in particular a developmental defect, comprising decreasing or increasing the expression in a gene of interest in a cell at any stage during the inventive method. A gene of interest can be a gene, that is suspected to be essential or detrimental when active during the development healthy neuronal tissue. Methods to decrease or increase expression in a gene are well known in the art, and include knock-out or knock-down methods (especially RNA interference, antisense inhibition, shRNA silencing, etc.), or introductions of transgenes (e.g. knock-in), respectively. Such decrease or increases can be conditional, e.g. by introducing a genetic construct with inducible promoters and/or conditional knock-out or knock-downs or knock-ins. The introduction of conditional mutations of essential genes or introductions of lethal genes are possible by using suitable conditional mutation vectors, e.g. comprising a reversible gene trap. Conditional mutations preferably facilitate reversible mutations, which can be reversed to a gene-active or inactive, respectively, state upon stimulation, e.g. as in the double-Flex system (WO 2006/056615 A1; WO 2006/056617 A1; WO 2002/88353 A2; WO 2001/29208 A1). Mutations can either be random or site-directed at specific genes. Thus in preferred embodiments of the invention, reversible mutations are introduced into the pluripotent stem cells, either by random (forward) or site directed (reverse) mutagenesis. Suitable vectors comprising insertion cassette with a reversible mutations. Mutations can be switched on or off at any stage of the inventive method. Vectors or other nucleic acids can be introduced into cells with any method known in the art, e.g. electroporation. It is of course also possible to provide cells having a given mutation. Such cells can be isolated from a patient, followed by a step of inducing pluripotent stem cell status, and letting the cells develop into the inventive tissue, e.g. by the method described above. The patient may have a particular disease of interest, especially a neurological defect or cerebral deformity. Such a method has been shown in the examples below for cells of a patient with microcephaly. Genetic mutations of microcephaly, such as a mutation in the gene Cdk5Rap2 leading to decreased expression, are example mutations, which can be investigated by the inventive method.

The present invention further provides a method of screening a candidate therapeutic agent suitable for treating a developmental neurological tissue defect of interest, comprising performing the above method for investigating a mutation and administering the candidate agent to said cells at any stage during the method, preferably at all stages. According to this aspect, a candidate therapeutic drug can be screened for having an effect on any cell with a mutation, which can be introduced as described above. It is of course also possible to use cells of patients with a given mutation, inducing pluripotent stem cell status and performing the inventive methods to induce tissue development as described above. In particular, the present invention provides investigations in mutations in microcephaly and allows the screening of pharmaceutical agents, which can affect the mutations, e.g. compensate for the insufficiency or overexpression in the mutated gene, e.g. Cdk5Rap2 in microcephaly. A positive candidate drug could be a compound, which restores normal cellular development, as can be observed by performing the inventive tissue generation method without a mutation for comparison, e.g. by using healthy pluripotent stem cells.

Of course, it is also possible to screen candidate drugs, e.g. candidate therapeutic drugs, to have any effect on normal tissue as well, without a mutation, which leads to an aberrant development. Thus in yet another aspect, the invention relates to a method of testing a candidate drug for neurological effects, comprising administering a candidate drug to an artificial culture and determining an activity of interest of the cells of said culture and comparing said activity to an activity of cells to the culture without administering said candidate drug, wherein a differential activity indicates a neurological effect. Any kind of activity of the inventive cells or tissue, including metabolic turn-over or neuronal signalling can be searched for in a candidate drug. In essence, the inventive highly differentiated tissue can be used as a model for cerebral behaviour testing on any effects of any drug. Such a method might also be used to test therapeutic drugs, intended for treating any kind of diseases, for having side-effects on nerves, in particular brain tissue, as can be observed in the inventive tissue culture.

The present invention can also be used to obtain neuronal cells. In particular, the invention provides a method of obtaining a differentiated neural cell comprising the step of providing an artificial culture and isolating a differentiated neural cell of interest, or comprising the step of generating an artificial tissue culture according to the invention further comprising the step of isolating a differentiated neural cell of interest. Such cells isolated from the inventive culture or tissue have the benefit of representing similar morphological properties as cells isolated from cerebral tissue of an non-human animal, as mentioned above, or a human.

The present invention further provides a kit for generating the inventive tissue culture comprising containers with any one of the culturing media described above, especially a medium containing a three dimensional matrix as described above and nutrients and a medium comprising retinoic acid and nutrients, optionally further comprising a medium comprising nutrients and a ROCK inhibitor and/or optionally comprising a medium comprising nutrients and lacking growth factors that would differentiate neural tissue to a particular fate.

The kit further comprises a medium C comprising a three dimensional matrix, and preferably lacking growth factors that would differentiate neural tissue to a particular fate. Such absent growth factors may be any one of Shh, Wnt, Bmp, retinoids, or FGF, or any combination thereof, especially all of them. This medium preferably further comprises cell nutrients. Especially preferred, the medium comprises N2 supplement (Price and Brewer. 2001), B27 supplement (Price and Brewer. 2001), insulin, 2-mercaptoethanol, glutamine, non-essential amino acids, or any combination thereof.

The kit further comprises a medium D comprising retinoic acid and nutrients. This medium preferably lacks the three dimensional matrix. Especially preferred, the medium comprises N2 supplement, B27 supplement, insulin, 2-mercaptoethanol, glutamine, non-essential amino acids, or any combination thereof. This medium preferably lacks growth factors that would differentiate neural tissue to a particular fate. Such absent growth factors may be any one of Shh, Wnt, Bmp, or FGF, or any combination thereof, especially all of them.

Optionally, the kit may further comprises a medium A comprising a ROCK inhibitor and nutrients. Especially preferred, the medium comprises serum replacement formulation, fetal bovine serum, glutamine, non-essential amino acids, 2-mercaptoethanol, bFGF, preferably about 4 ng/ml bFGF, or any combination thereof.

Optionally, the kit may further comprise medium B comprising nutrients and lacking growth factors that would differentiate neural tissue to a particular fate. Such absent growth factors may be any one of Shh, Wnt, Bmp, retinoids, or FGF, or any combination thereof, especially all of them. Especially preferred, the medium comprises N2 supplement (Price and Brewer. 2001), glutamine, non-essential amino acids, heparin, or any combination thereof.

The inventive kit preferably comprises a medium for any one of the steps described above, selected from the step of culturing pluripotent stem cells, the step of culturing the aggregate of pluripotent stem cells, the step of culturing in a three dimensional matrix, preferably a gel, the step of in a suspension culture, preferably a bioreactor. In particular preferred this the combination of a medium for the step of culturing in a three dimensional matrix, preferably a gel, and the step of in a suspension culture; or a combination of a medium for the steps of the step of culturing the aggregate of pluripotent stem cells, the step of culturing in a three dimensional matrix, preferably a gel. Preferably, the media for performing separate steps are provided in separate containers, such as vials or flasks. Any one of the inventive medium may comprise further auxiliary substances such as buffers, stabilizers, nutrients, as mentioned above. The medium may be provided in a solid, dry form or in aqueous form.

It is contemplated that any method or product described herein can be implemented with respect to any other method or product described herein and that different embodiments may be combined.

The claims originally filed are contemplated to cover claims that are multiply dependent on any filed claim or combination of filed claims.

The use of the word "a" or "an" when used in conjunction with the term "comprising" in the claims and/or the specification may mean "one", but it is also consistent with the meaning of "one or more", "at least one", and "one or more than one".

It is contemplated that any embodiment discussed herein can be implemented with respect to any method or product of the invention, and vice versa. Any embodiment discussed with respect to a particular condition can be applied or implemented with respect to a different condition. Furthermore, compositions and kits of the invention can be used to achieve methods of the invention.

Throughout this application, the term "about" may be used to indicate that a value includes the standard deviation of error for the device or method being employed to determine the value or in a set value may refer to ±10%.

The present invention is further illustrated by the following figures and examples, without being restricted to these embodiments of the invention.

FIGURES

FIG. 1. Description and characterization of the cerebral organoid culture system. a. Schematic of the culture system described in more detail in Methods. Human pluripotent stem cells (hPSCs) were dissociated from colony culture on feeders and transferred to floating aggregates termed embryoid bodies which begin differentiating into the three germ layers. These were allowed to grow for 6 days in media containing low bFGF, and then transferred to low adhesion plates containing a defined neural induction media to support neuroectoderm growth while limiting growth of other germ layers. On day 11, neuroectoderm tissues were transferred to Matrigel droplets and grown in floating culture in differentiation media followed by culture in a spinning bioreactor in differentiation media containing retinoic acid (RA). Example images of each stage are shown below the schematic. b. Neuroepithelial tissues generated using this approach (left panel) were larger and more continuous than when grown in stationary suspension without Matrigel (right panel). This approach also generated tissues with larger fluid filled cavities as well as typical apical localization of the neural N-cadherin protein (arrow). c. Sectioning and immunohistochemistry revealed that advanced tissues displayed complex morphology with heterogeneous regions of neural tissues containing neural progenitors (Sox2, red) and neurons (Tuj1, green) (arrow). d. Low magnification bright field imaging further revealed large fluid-filled cavities reminiscent of ventricles (white arrow) as well as a variety of developing neural tissues including retina, as indicated by the presence of a retinal pigmented epithelium (black arrow). e. Hemotoxylin-eosin staining of cerebral organoids compared with stationary culture reveals overall larger tissues with substructure reminiscent of brain regions such as forebrain cortex (arrows) and choroid plexus (arrowhead).

Figure 2:
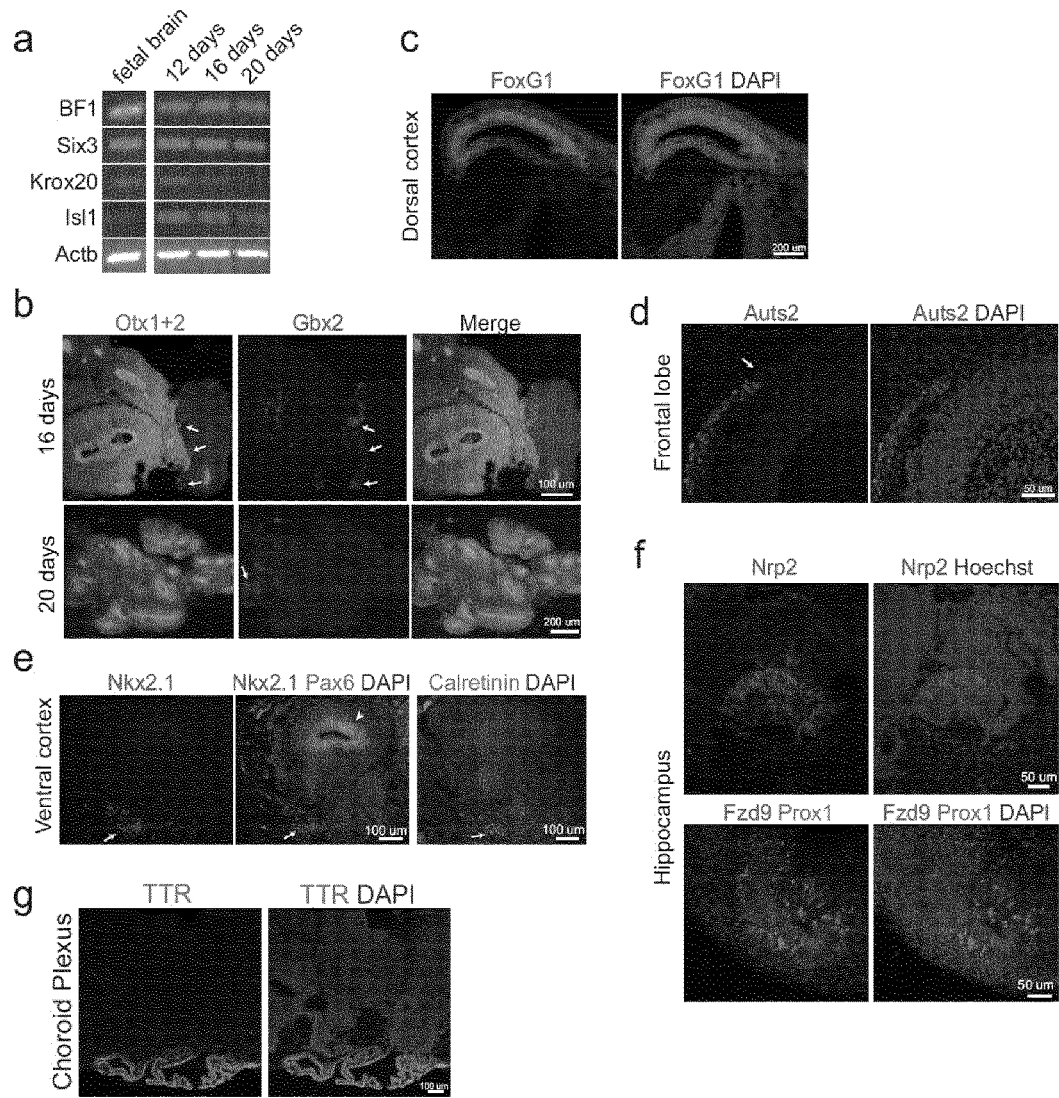

FIG. 2. Human cerebral organoids recapitulate various brain region identities. a. RT-PCR for forebrain markers (BF1 and Six3) as well as hindbrain markers (Krox20 and Isl1) in cortical organoids at 12, 16 and 20 days of differentiation. Human fetal brain cDNA was used as a positive control. b. Immunohistochemistry for the forebrain/midbrain markers Otx1/2 (green) and the hindbrain marker Gbx2 (red) at 16 and 20 days of differentiation revealing primarily fore/midbrain identity with adjacent regions of hindbrain reminiscent of the mid-hindbrain boundary (arrows). DAPI marks nuclei (blue). c. Immunohistochemistry for the marker FoxG1 (red) revealing a discrete region of dorsal cortex within the organoid. d. Staining for the marker of frontal lobe Auts2 (red) revealing subregionalization of cerebral cortical lobes within the organoid. e. Staining for Nkx2.1 (red), a marker of ventral cortical identity, and Pax6 (green) marking dorsal cortex reveals adjacent dorsal and ventral regions. Staining for Calretinin (green) in a serial section reveals the production of cortical interneurons in the ventral region of the organoid. f. Staining for Neuropilin-2 (Nrp2, red) as well as costaining of Frizzled-9 (red) and Prox1 (green) revealing hippocampal regions within independent cerebral organoids. g. Immunohistochemical staining for Transthyretin (TTR) a marker of choroid plexus, revealing regions which also display typical morphology of the choroid plexus.

Figure 3:
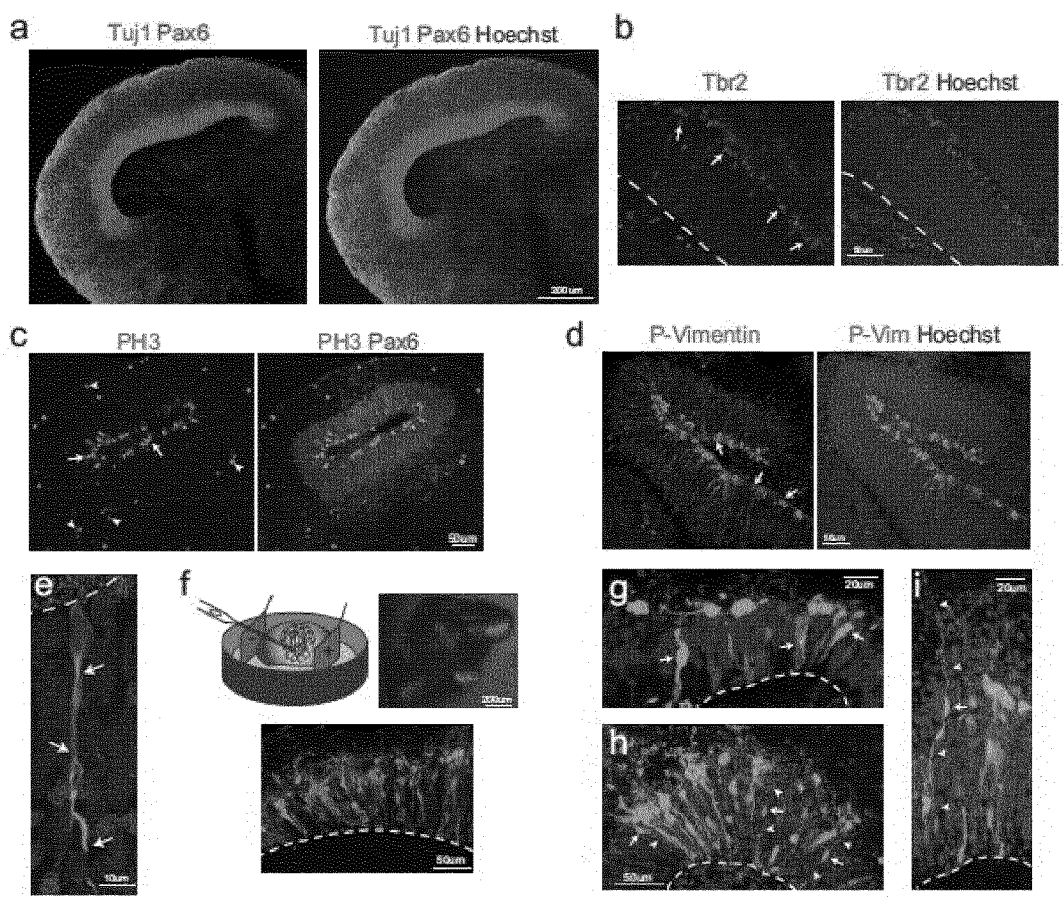

FIG. 3. Stereotypical organization of progenitor zones in dorsal cortex of cerebral organoids. a. Immunohistochemistry for neurons (Tuj1, green) and radial glial progenitors (Pax6, red) in a typical large (approx. 1 mm across) dorsal cortical region within a cerebral organoid that recapitulates the apical-basal organization of progenitors adjacent to the fluid-filled cavity in a region reminiscent of ventricular zone and newborn neurons accumulating basally. b. Staining for the IP marker Tbr2 (red) revealing a subventricular zone localization much like in vivo. c. Staining for phosphohistone H3 (PH3, green) to mark cells in mitosis. Progenitor divisions primarily occurred at the apical surface, but several divisions can be seen is a subventrical region, likely belonging to IPs or oRGs. Pax6 (red) marks radial glia. d. Immunohistochemistry for phospho-Vimentin (green), a marker of mitotic radial glia revealing typical division at the apical surface. e. Higher magnification image of phospho-Vimentin staining (green) of a dividing readial glia revealing the long basal process typical of radial glial morphology. f. Schematic of electroporation technique. Plasmid DNA was injected into fluid-filled cavities within the organoid and an electric pulse was applied to electroporate cells (radial glial progenitors) adjacent to the cavity. These results in several regions of electroporation (right panel, GFP in green) and high efficiency of electroporation of RGs (lower panel, GFP in green). g. GFP electroporated progenitors (arrows) in an early stage tissue (18 days) revealing neuroepithelial morphology. h. GFP electroporated tissue at 30 days revealing radial glia (arrows) with typical bipolar morphology (arrowheads). i. GFP electroporated tissue at 36 days revealing more advanced thicker cortical region with radial glia (arrow) exhibiting long apical and basal processes (arrowheads).

Figure 4:
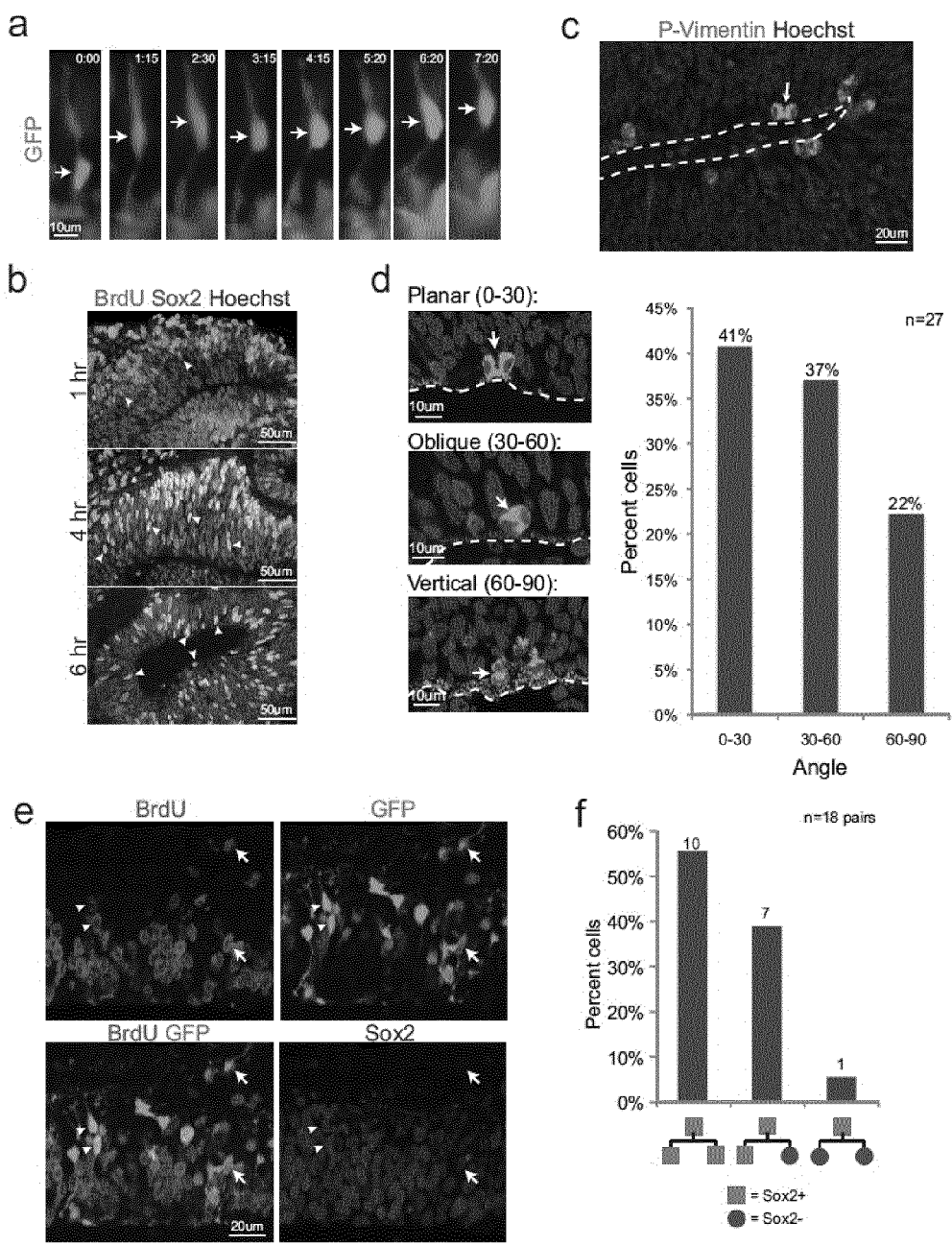

FIG. 4. Radial glia of cerebral organoids exhibit typical characteristics seen in vivo. a. Frames from live imaging of an electroporated radial glia (GFP, green) showing movement of the cell body (arrow) along the bipolar processes. Time in hours and minutes is shown in upper right. b. BrdU pulse-chase experiment revealing interkinetic nuclear migration. At 1 hour of BrdU administration, BrdU positive (green) radial glia (Sox2, red) were located in the basal region of the VZ. 4 hours after washing out BrdU, many BrdU+ cells can be seen shifted apically, while at 6 hours after washing, several cells can be seen at the apical surface. c. Phospho-Vimentin (green) staining revealing a mitotic cell at the apical surface during anaphase (arrow) with a planar orientation of division. d. Quantification of radial glial orientation of division relative to the apical surface, displayed in bins of 0-30 degrees (planar), 30-60 degrees (oblique) and 60-90 degrees (verticle). n=27 cells from 5 different cerebral cortical regions. e. Lineage tracing in GFP electroporated tissues following a short one hour pulse of BrdU followed by a 16-hour chase. Daughter cell pairs are marked by colabeling with GFP and BrdU. Symmetric divisions with daughter cells of the same identity (Sox2 positive, blue, arrowheads) as well as asymmetric divisions (arrows) can be observed. f. Quantification of results shown in e. for 18 cell pairs from three independent cortical tissues. Numbers above bars represent number of daughter pairs for each category.

Figure 5:
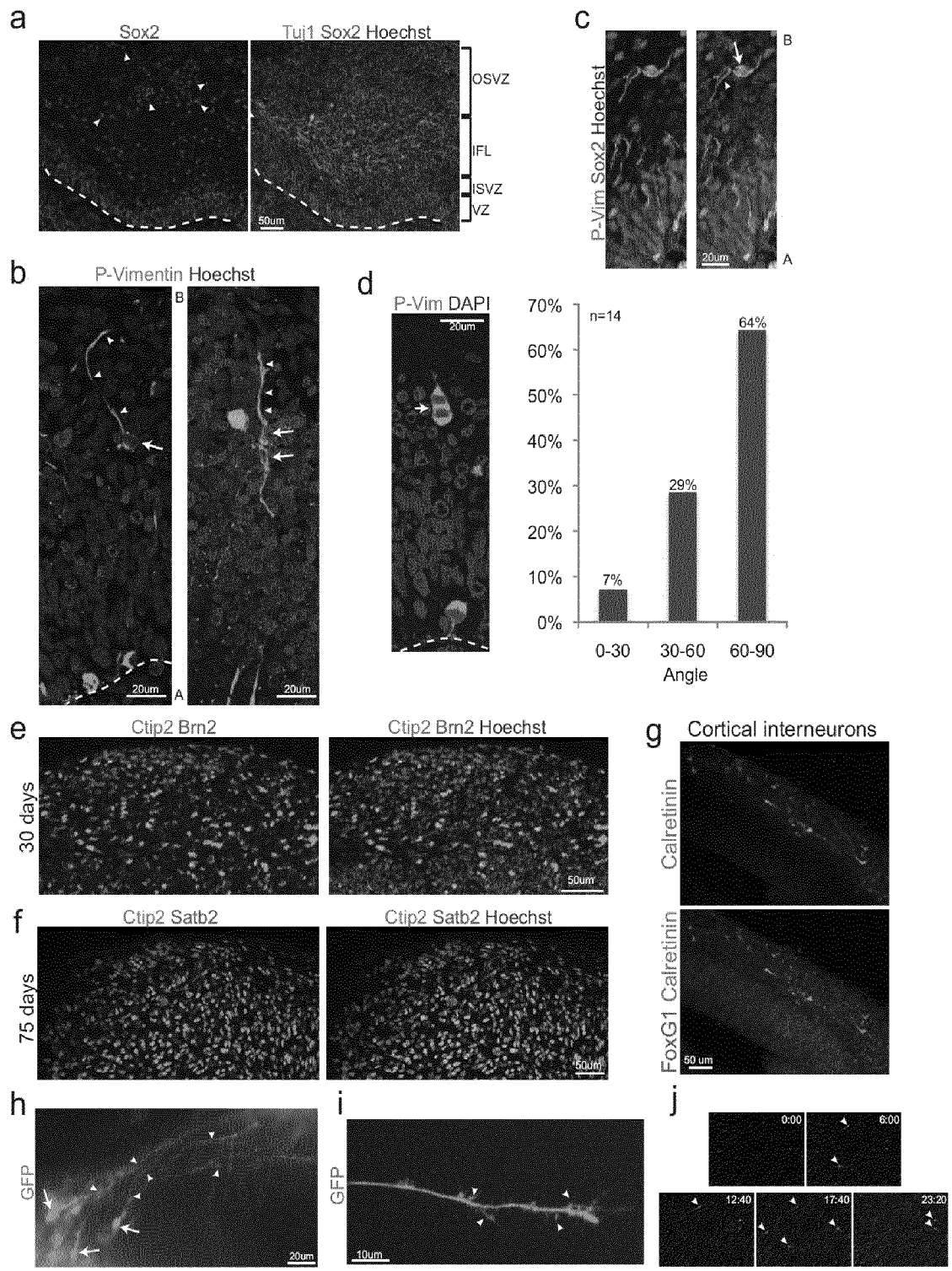

FIG. 5. Cerebral organoids produce oRGs and neurons with typical morphology and migration behavior. a. Staining for Sox2 (red, radial glia) and Tuj1 (green, neurons and processes) reveals the presence of outer radial glia separated from the apical ventricular zone (VZ) and organized similar to human cortical development. The VZ and SVZ appear separated from a layer of oRGs (OSVZ) by a layer of Tuj1+ fibers much like the inner fiber layer (IFL). b. Immunohistochemistry for phospho-Vimentin (green) revealing dividing oRGs (arrows) with typical cell morphology, namely the presence of a basal process (arrowheads) but lacking an apical process. Just after division a daughter cell pair can be seen, one of which inherits the basal process. Apical (A) is oriented down while basal (B) is oriented up. c. Staining for phospho-Vimentin (green) in a recently divided daughter cell pair reveals one daughter maintained as an oRG (Sox2+, red) while the other lacks Sox2 expression (arrowhead). d. Orientation of division of a mitotic oRG in anaphase revealing vertical (60-90 degrees) orientation relative to the apical surface (dashed line). Quantification of this orientation is shown on the right. e. Immunohistochemistry for the early born neuron marker Ctip2 (green) and later born neuron marker Brn2 (red) reveals independent neuron populations exhibiting rudimentary separation at 30 days of differentiation. f. At 75 days of differentiation, separation of early born (Ctip2, green) and late born (Satb2, red) is more evident with inside-out organization reminiscent of that seen in vivo. g. Calretinin staining (green) for cortical interneurons generated from ventral cortex (FIG. 2e) exhibit typical morphology of tangential migration into the dorsal cortical tissue (FoxG1, red) with leading processes perpendicular to the apical "ventricular" surface. h. GFP (green) electroporated cortical neurons (arrows) extend long-range axons with evidence of axon bundling (arrowheads) similar to that seen in pyramidal tracts. i. High magnification image of GFP (green) electroporated neural axon displaying complex morphology and axon branching (arrowheads). j. False color heat map frames from live imaging with Fluo-4 calcium sensitive dye revealing spontaneous calcium surges in individual neurons (arrowheads) of cerebral organoid. Time is displayed in minutes:seconds.

Figure 6:
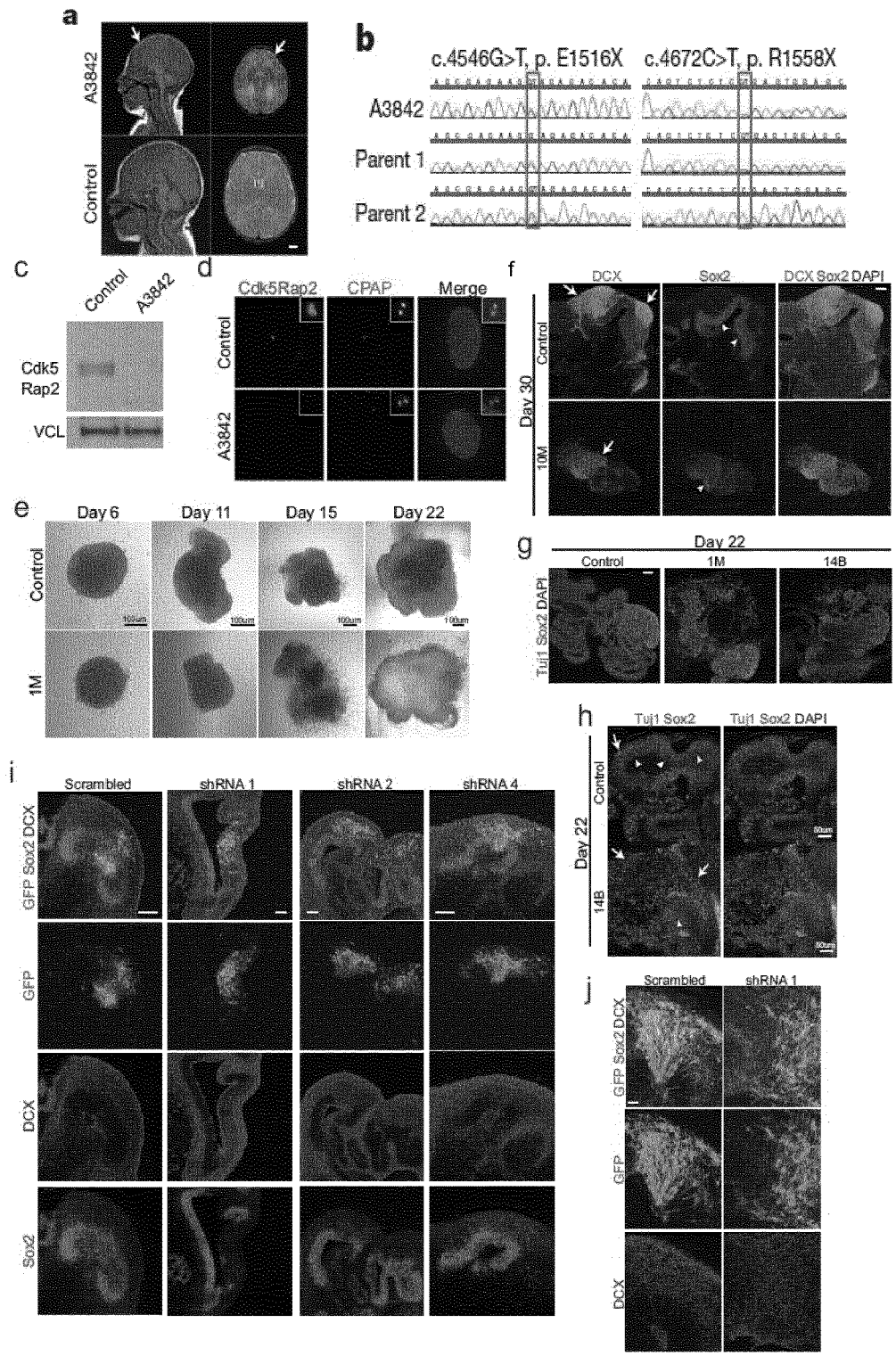
Figure 9:
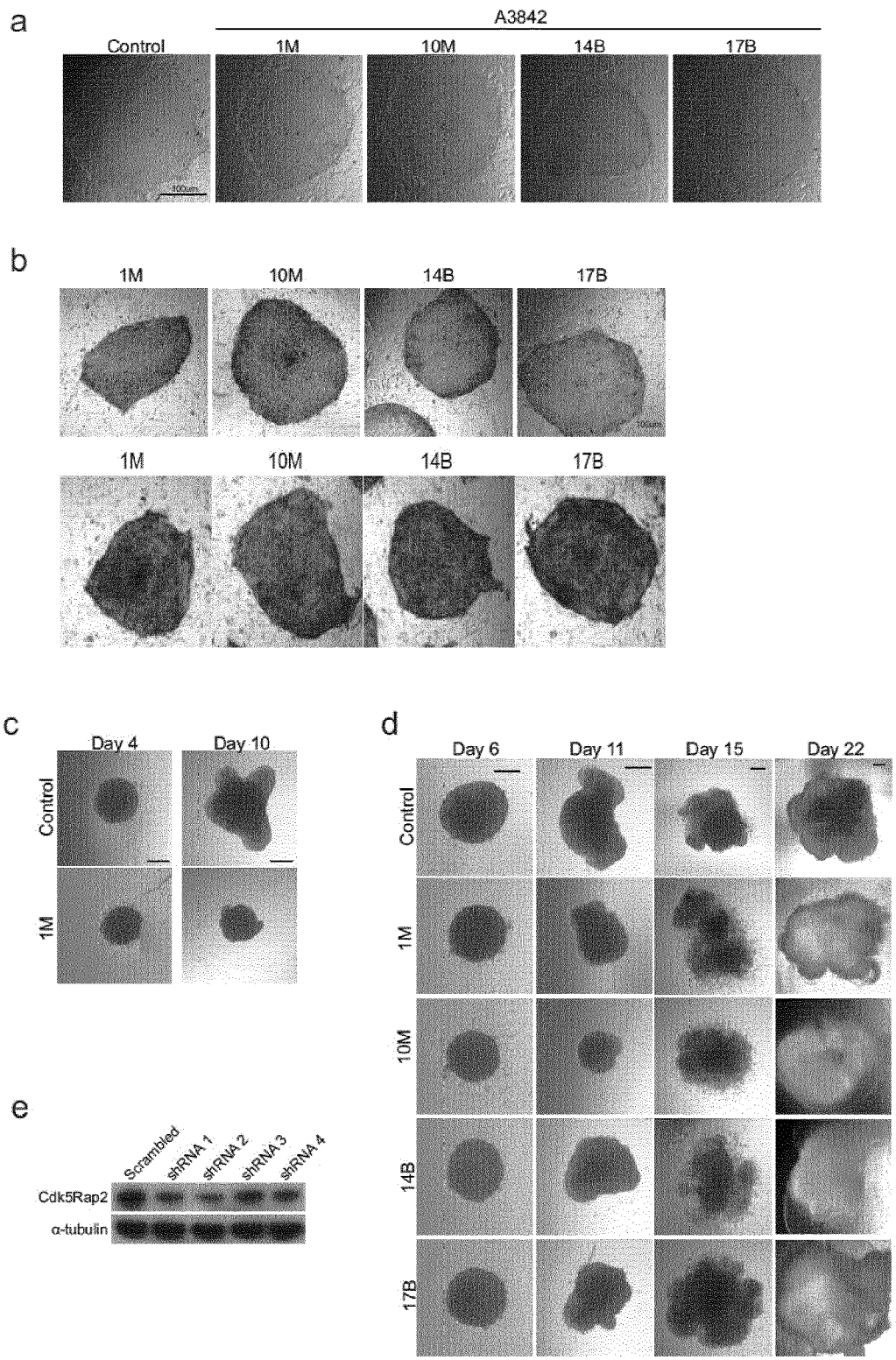

FIG. 6. Cerebral organoids generated from a patient derived iPSCs or shRNA electroporation model microcephaly a. MRI scan from patient A3842 taken at birth (top) compared with age-matched control (bottom) showing brain and head size reduction and simplified cortical folding (arrows). Saggital T1 (left) and axial T2 (right) images. Scale bar 1 cm. b. Sequencing chromatograms demonstrating compound heterozygous nonsense mutations inherited from each parent. c. Western blot for Cdk5Rap2 protein in lysates from control and patient (A3842) skin fibroblasts revealing loss of the protein in A3842 patient. Vinculin (VCL) is shown as a loading control. d. Immunocytochemical staining for Cdk5Rap2 in patient (A3842) and control fibroblasts revealing localization to centrosomes (CPAP, green) in control but lack of staining in patient fibroblasts. e. Representative bright-field images of cerebral organoids generated from control iPSCs and patient derived (line 1M is shown here, all lines are shown in FIG. 9) at 6, 11, 15, and 22 days of differentiation. Control exhibits large fluid-filled cortical regions, while patient derived tissue exhibits increased outgrowth with fewer regions of thick cortical tissue. f. Immunohistochemistry in Control and patient derived (Line 10M is shown as a representative example) tissues at day 30 of differentiation revealing fewer neurons (Doublecortin, DCX, green, arrows) and smaller progenitor zones (Sox2, red, arrowheads). g. Staining at an earlier stage (day 22) for neurons (Tuj1, green) and radial glia (Sox2, red) revealing smaller progenitor zones and increased neurons in patient derived tissues (Lines 1M and 14B are shown here). h. Higher magnification of developing cortical tissues showing increased neurons (Tuj1, green, arrows) in patient derived (line 14B) tissue. i. hES cell derived organoids co-electroporated with GFP (green) and shRNAs against Cdk5Rap2 or a scrambled shRNA. Regions electroporated with Cdk5Rap2 shRNAs exhibit loss of Sox2+(red) progenitors and increased doublecortin (DCX, blue) neurons. j. Higher magnification of results in i. showing neuronal morphology of GFP (green) electroporated with Cdk5Rap2 shRNA. These exhibit increased DCX (blue) expression and a loss of Sox2 (red) compared with scrambled or adjacent non-electroporated tissue.

FIG. 7. Generation of cerebral organoids from multiple human pluripotent stem cells. a. Hemotoxylin-eosin staining of organoids generated from human H9 ES cells as well as human iPS cells display similar size and complex morphology as well as the presence of advanced forebrain tissues, shown at higher magnification in the lower panels. b. Staining for N-cadherin (green) and newborn neurons (Doublecortin, DCX, red) in tissues generated from both human H9 ES cells and human iPS cells reveals similar organization and in tact apical basal polarity in both types of tissues.

Figure 8:
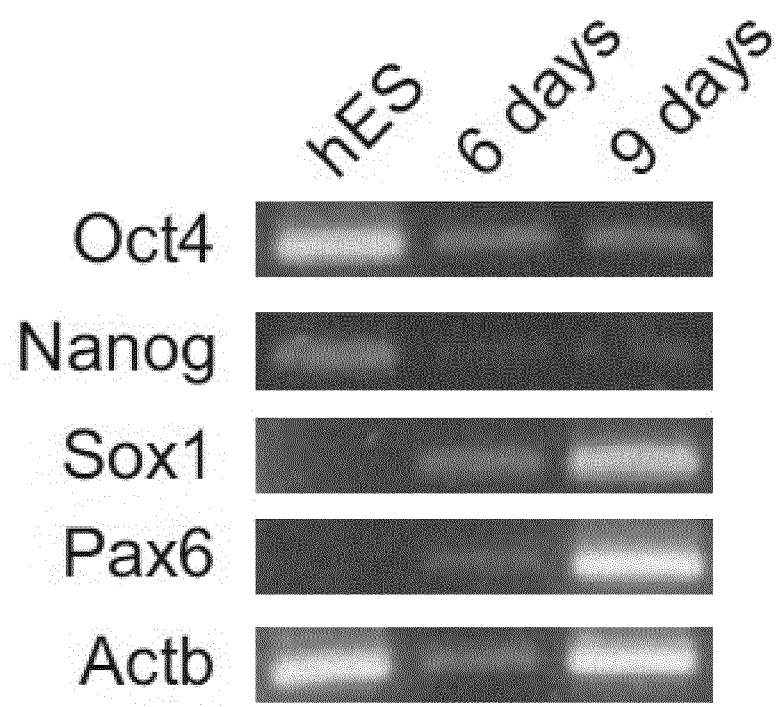

FIG. 8. Neural identity during differentiation of cerebral organoids. RT-PCR of the pluripotency markers Oct4 and Nanog as well as neural identity markers Sox1 and Pax6 in undifferentiation human ES cells and following differentiation at 6 and 9 days revealing decreased pluripotent identity at 9 days of differentiation whereas neural identity was activated.

FIG. 9. Characterization of patient derived iPSCs and cerebral organoids. a. iPS cells derived from A3842 patient skin fibroblasts exhibit typical ES cell-like morphology. Four lines were chosen for analysis based on this typical morphology and pluripotency. b. Alkaline phosphatase staining (blue) of patient derived iPS cell colonies revealing pluripotency. c. Representative early organoid culture of patient (line 1M) and control using the protocol and timing established for normal hES cells. Patient tissues were much smaller and failed to thrive so the protocol had to be slightly modified to produce neural tissues. d. Patient derived tissues using increased starting cell number display neuroepithelium but do not form thick fluid-filled cortical tissues as seen in control derived tissues. e. Western blot for endogenous Cdk5Rap2 in 293T cells transfected with 4 different shRNAs against Cdk5Rap2. shRNA1 and 2 are most efficient while shRNA 4 leads to a modest reduction in protein. Tubulin is shown as a loading control.

Figure 10:
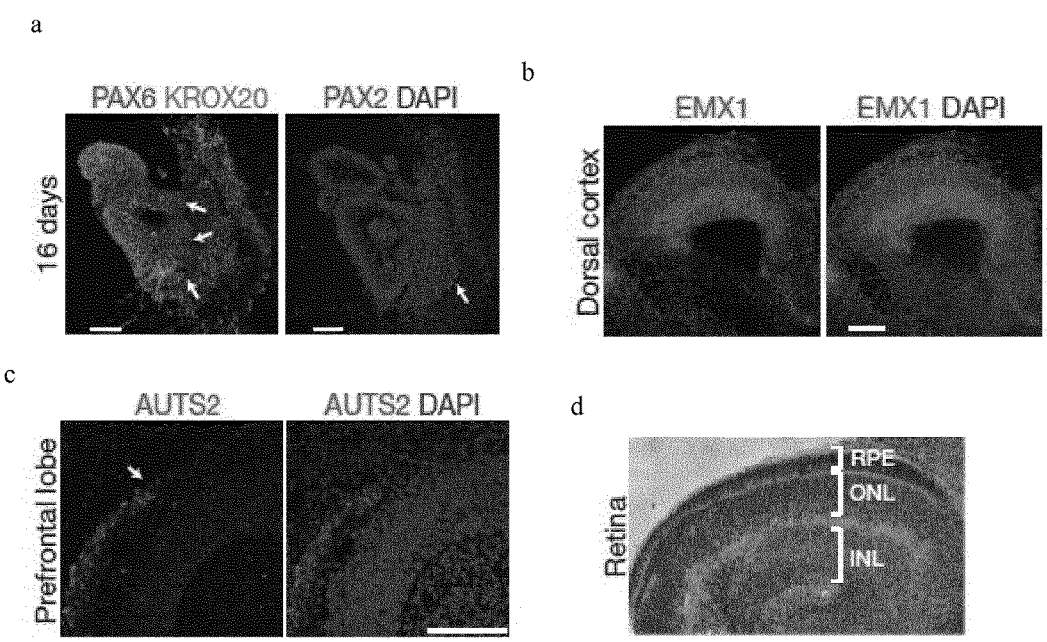

FIG. 10. Human cerebral organoids recapitulate various brain region identities. a. Staining for the preplate marker Tbr1 (red) and neuronal marker MAP2 (green) revealing superficial preplate (upper bracket) and underlying neuronal IZ-like layer (lower bracket). b-c. Staining for various brain region identities: forebrain (b); prefrontal cortex (note the discrete boundary, arrow), Auts2 (c); hippocampus, Nrp2, Fzd9, Prox1. d. Hematoxylin-eosin staining of retinal tissue exhibiting stereotypical layering: retinal pigment epithelium (RPE), outer nuclear layer (ONL) and inner nuclear layer (INL). Scale bars: 100 µm.

FIG. 11. Stereotypical organization and behavior of progenitors. a. Staining for the preplate marker Tbr1 (red) and neuronal marker MAP2 (green) revealing superficial preplate (upper bracket) and underlying neuronal IZ-like layer (lower bracket). b. Staining for the IP marker Tbr2 (red) revealing SVZ localization of IPs (arrows).

Figure 12:
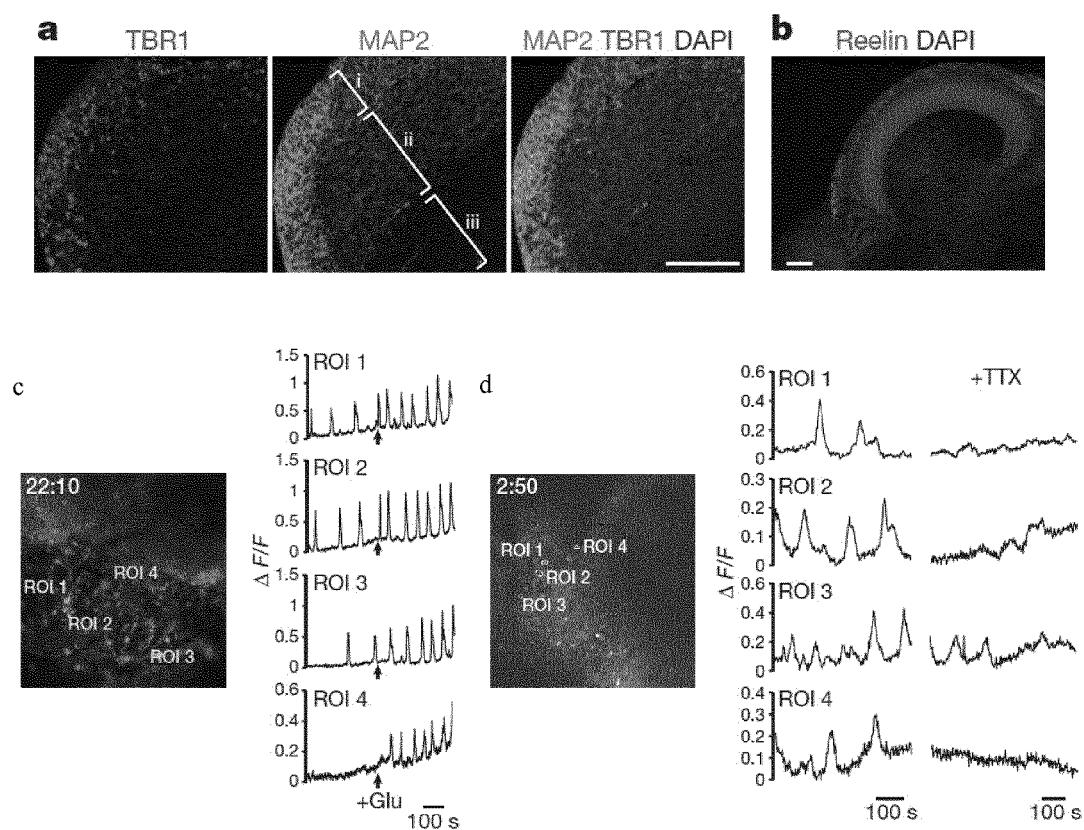

FIG. 12. Organization and maturation of cerebral cortical neurons. a. Immunohistochemical staining at day 30 showing preplate (Tbr1) with early signs of radial organization (MAP2, bracket i) and the presence of an IZ-like layer (bracket ii) adjacent to the VZ/SVZ (bracket iii). DAPI marks nuclei (blue). b. Reelin staining indicating Cajal-Retzius cells along the basal surface of dorsal cortical tissue. c. Single cell tracings of calcium surges with glutamate application (regions of interest, ROI, outlined in left panel) as measured by change in fluorescence (arbitrary units). Arrows mark the time of addition of glutamate. d. Single cell tracing (ROIs marked in image at left) of calcium surges before (left panels) and after the addition of TTX (right panels). Scale bars: 100 µm.

Figure 13:
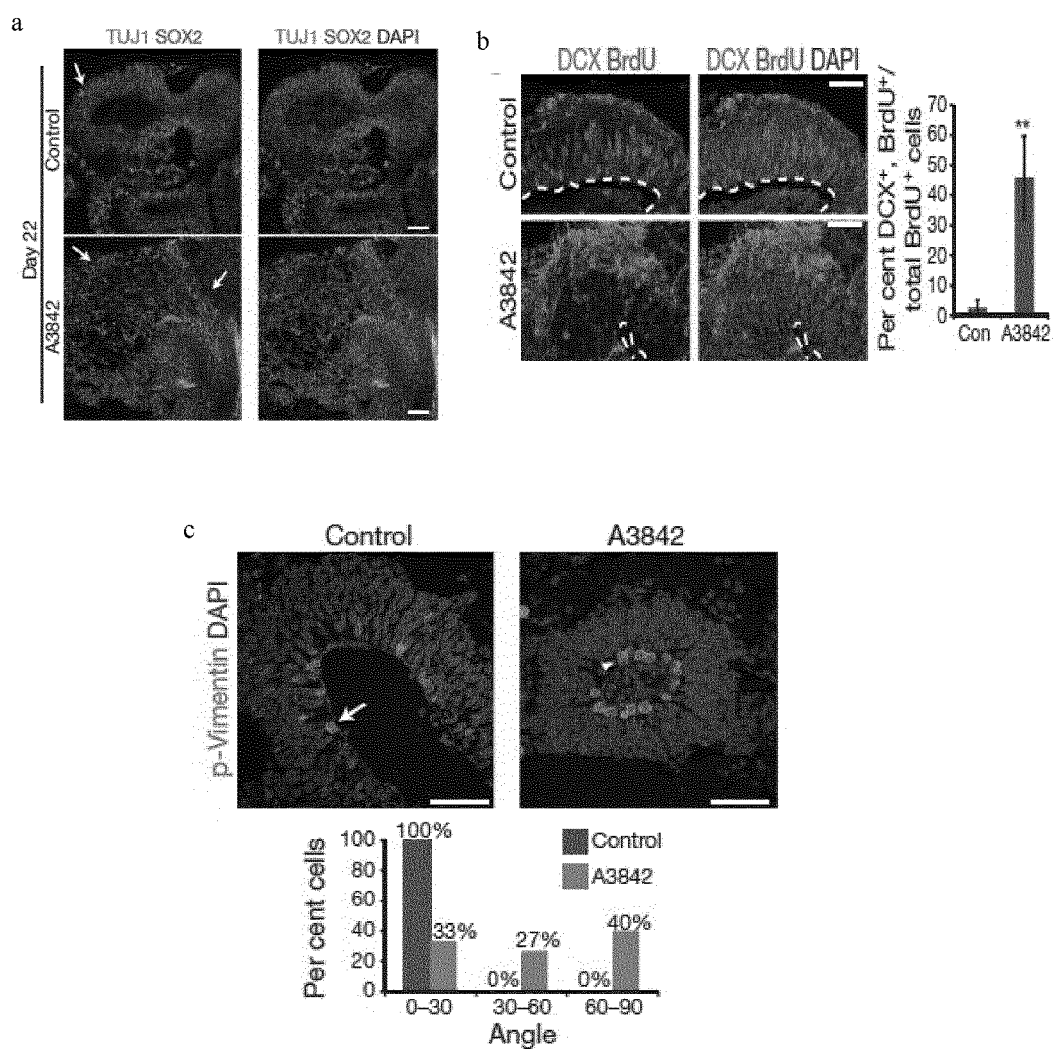

FIG. 13. Cerebral organoid modeling of microcephaly.
a. Staining at day 22 showing increased neurons (Tuj1, arrows) in patient-derived tissue (14B). b. BrdU pulse-chase in control and patient-derived organoids (14B) showing higher percentage of BrdU cells with neural identity and less in the VZ compared with control. Results quantified at right. Error bars are S.D. **$P<0.01$, Student's t-test. n=3 organoids for each condition (300 cells total for control, 204 cells for patient). c. P-Vimentin staining in control and patient-derived tissues (14B) showing RG mitotic divisions. Control RGs at anaphase divided exclusively horizontal (0-30 degree angle, arrow) whereas patient RGs displayed many oblique and vertical orientations (arrowhead). Results quantified at right (P<0.01, 2×3 Fisher's exact test, n=11 cells for control, n=15 cells for patient-derived, from >5 cortical regions each).

Figure 14:
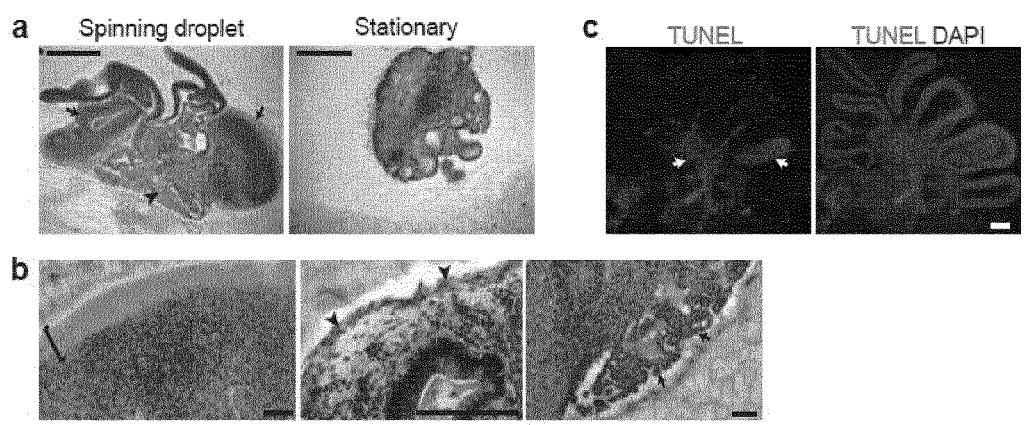

FIG. 14. Generation of cerebral organoids from multiple human pluripotent stem cells. a. Hemotoxylin-eosin staining of cerebral organoids compared with stationary culture reveals overall larger tissues with substructure reminiscent of brain regions such as forebrain cortex (arrows) and choroid plexus (arrowhead). b. Higher magnification images of hemotoxylin-eosin stained organoids revealing layering reminiscent of the cerebral cortical molecular layer (bar), as well as tissue reminiscent of meninges (arrowheads) and choroid plexus (arrows). c. TUNEL staining (green) revealing cell death in the interior regions (arrows) of the cerebral organoid with cortical regions developing along the exterior. DAPI marks nuclei (blue)

Figure 15:
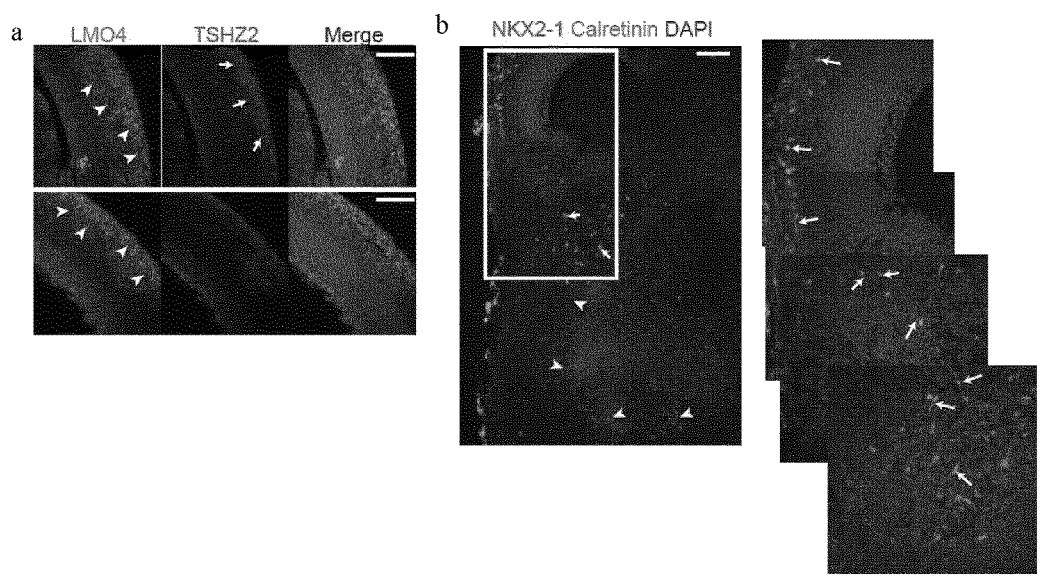

FIG. 15. Neural identity during differentiation of cerebral organoids. a. Staining for the cortical lobe markers Lmo4 (frontal and occipital marker, green) and Tshz2 (occipital marker, red). Note the expected nuclear staining (arrows, arrowheads) for both in one region (upper panels) suggesting occipital identity, while only Lmo4 staining (arrowheads) is clearly evident in another region (lower panels) suggesting frontal identity. DAPI marks nuclei (blue). b. Staining for the ventral marker Nkx2.1 (red) and the cortical interneuron marker Calretinin (green) on an organoid containing both ventral (arrowheads) and dorsal (upper left) regions within one section. Images at right are higher magnification stitched images of the region outlined in the lower magnification image at left. Calretinin interneurons can be seen between the two regions with typical morphology of migration and redirection toward the dorsal cortex (arrows). Scale bars: 100 μm.

Figure 16:
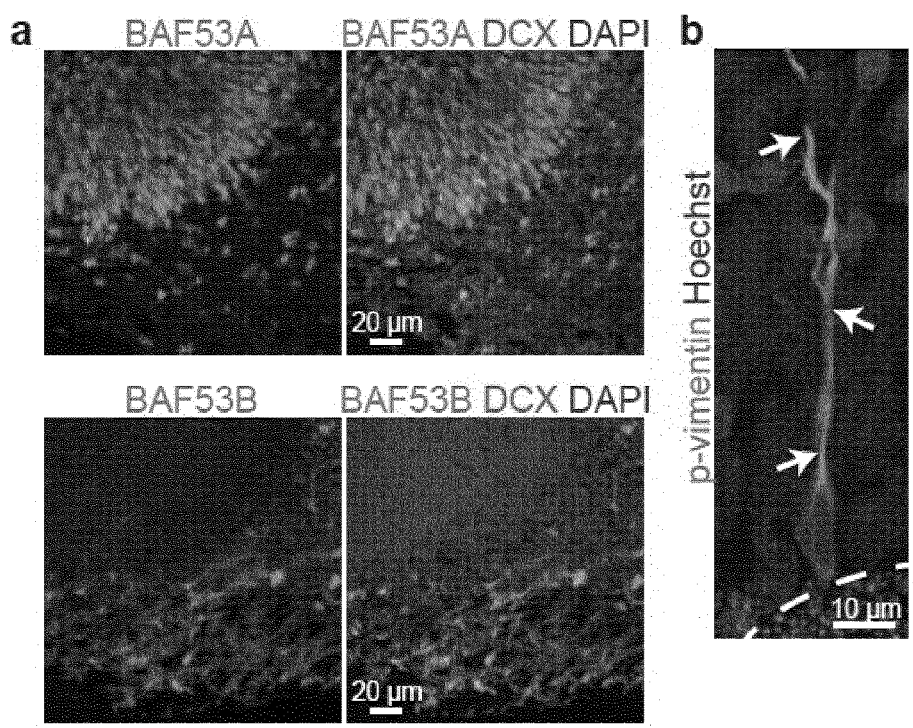

FIG. 16. Radial glial organization and morphology. a. Staining for the chromatin remodeling BAF components Baf53a (green, upper panels) and Baf53b (green, lower panels) in serial sections of the same tissue showing the neural progenitor-specific Baf53a expressed in VZ RGs while the neuron-specific Baf53b is expressed in DCX+ (red) neurons outside the VZ. b. Higher magnification image of phospho-Vimentin staining (green) of a dividing radial glia revealing the long basal process typical of radial glial morphology.

FIG. 17. Spatial organization and characteristics of cortical neuron identities. a. Staining for the preplate marker Tbr1 (green) and the deep-layer marker Ctip2 (red) at day 30 revealing rudimentary spatial separation reminiscent of the early stages of CP development. b. Single cell tracings of calcium surges in individual neurons (regions of interest, ROI, outlined in left panel) as measured by change in fluorescence (arbitrary units).

Figure 18:
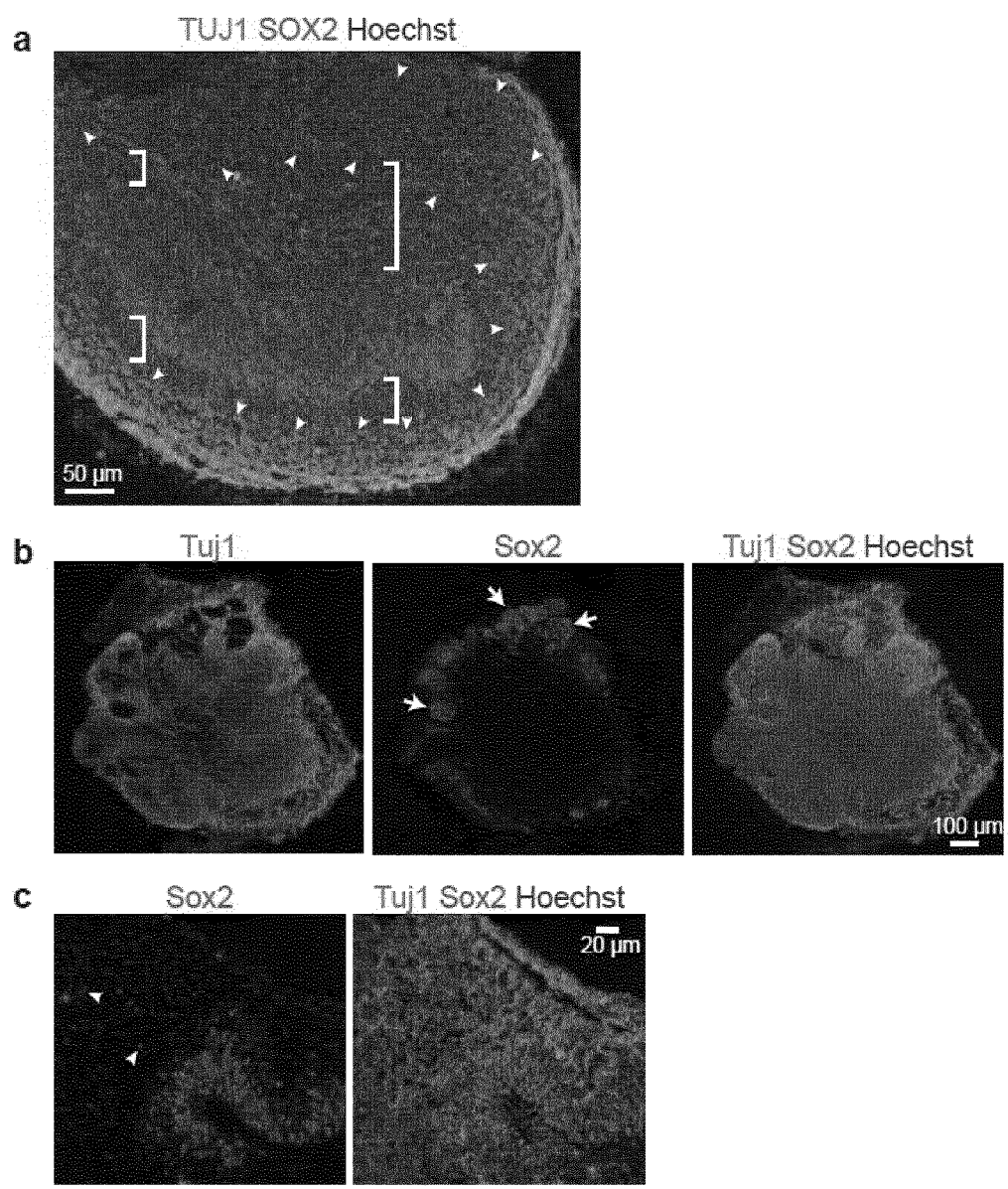

FIG. 18. Human features of cortical development not recapitulated in mouse organoids. a. Low magnification image of the region shown in FIG. 5a revealing the presence of a separated region of oRGs (demarcated by arrowheads) that appear separate from the VZ in all regions (brackets) but more separated and with a layer of Tuj1+ fibers in between in thicker parts of the cortical tissue (larger bracket). The entire organoid can be seen in FIG. 1c. b. Low magnification image of a cerebral organoid derived from mouse ESCs stained for neurons (Tuj1, green) and neural progenitors (Sox2, red) revealing overall smaller organoid size as well as smaller cortical regions (arrows) than human. c. Higher magnification of a region of cortical identity in mouse cerebral organoids stained for RG progenitors (Sox2, red) revealing the presence of only a few oRGs (arrowheads) that do not organize into a separate layer such as that seen in human.

Figure 19:
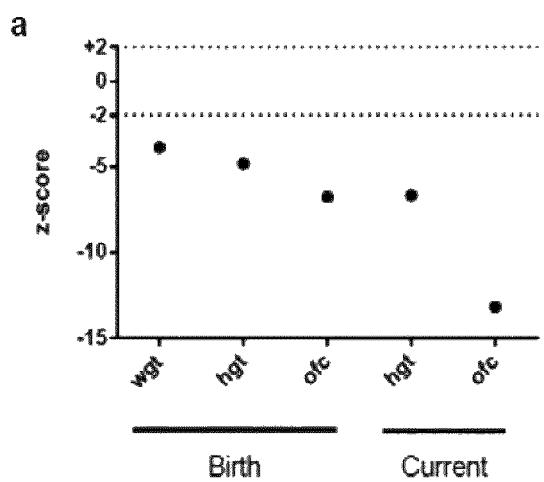

FIG. 19. Patient growth parameters. a. All growth parameters were significantly reduced both at birth and postnatally, with all z-scores less than −2 standard deviations from the population mean for age and sex (dashed line). Weight (wgt), height (hgt) and head circumference (occipitofrontal circumference, ofc) at birth and at current age of 3½ years of age. Head circumference was much more severely affected than height and weight, indicating that brain volume was disproportionately reduced as a result of more severe growth restriction.

Figure 20:
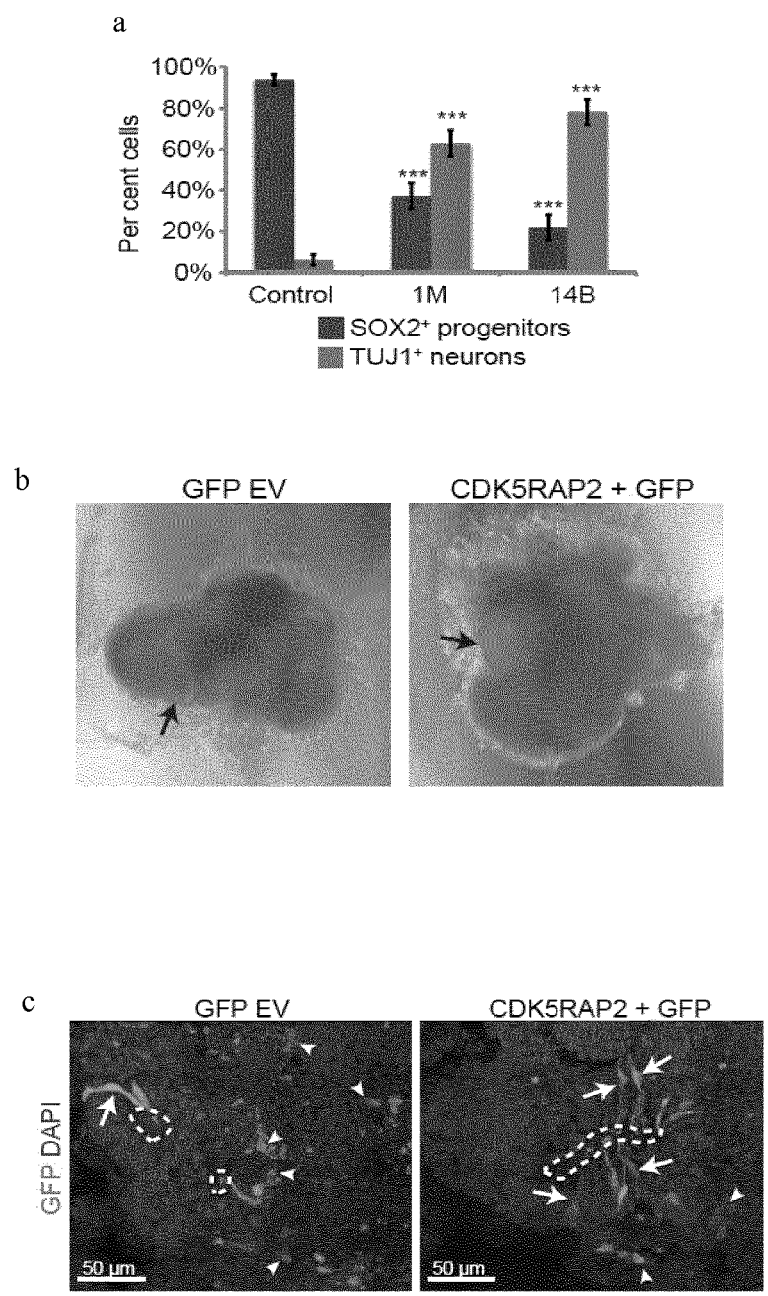

FIG. 20. Characterization of patient derived iPSCs and cerebral organoids. a. Quantification of the percentage of Sox2+ progenitors and Tuj1+ neurons in cerebral cortical regions of control and 2 lines of patient derived tissues (1M and 14B) at the early stage of day 22. Error bars are S.E.M. ***P<0.001 compared with control, Student's t-test. n=4 tissues for each line. b. Bright-field image of patient-derived tissues (line 14B) electroporated with either GFP alone (left panel) or GFP and CDK5RAP2 expression construct (right panel). Note the presence of larger neuroepithelial tissue (arrows) in CDK5RAP2 electroporated tissue compared with control. c. GFP staining (green) in GFP control (left panel) and CDK5RAP2 coelectroporated patient-derived tissues (14B) revealing the presence of multiple GFP+ neurons (arrowheads) in control 6 days after electroporation, whereas CDK5RAP2 electroporated tissues display multiple GFP+ radial glia (arrows).

Figure 21:
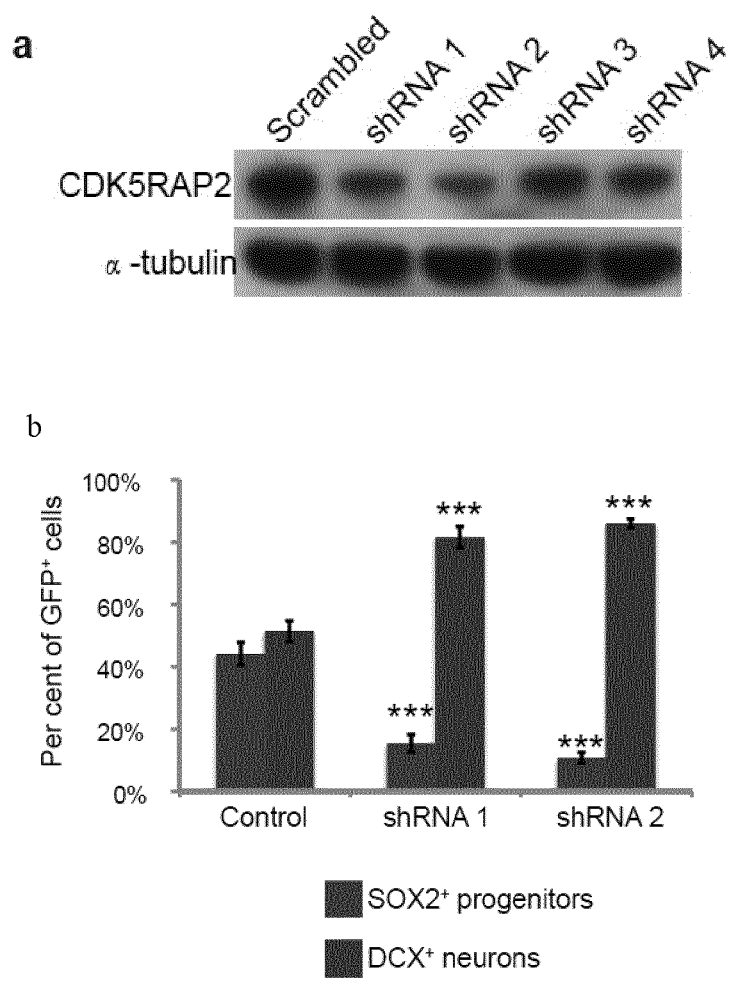

FIG. 21. shRNA mediated knockdown of CDK5RAP2 in human organoids. a. Western blot for endogenous CDK5RAP2 in 293T cells transfected with 4 different shRNAs against CDK5RAP2. shRNA1 and 2 are most efficient while shRNA 4 leads to a modest reduction in protein. Alpha-Tubulin is shown as a loading control. b. Quantification of percentage of GFP+ electroporated cells exhibiting Sox2+ progenitor identity or DCX+ neuronal identity in scrambled control or shRNA coelectroporated tissues. ***P<0.001 compared to control, Student's t-test, n=4 tissues for each shRNA. Error bars are S.E.M.

EXAMPLES

Example 1: Methods

Plasmid Constructs and Materials

GFP plasmid used for coelectroporation with shRNA and for live imaging was pCAG-GFP (Addgene plasmid 11150). shRNAs targeting human CDK5RAP2 were cloned using pSuper shRNA expression strategy (OligoEngine). Targeting sequences were as follows: shRNA 1 AGGACGTGTT-GCTTCAGAAAT (SEQ ID NO: 1), shRNA 2 AGAGTCA-GCCTTCTGCTAAAG (SEQ ID NO: 2), shRNA 3 GTGGAAGATCTCCTAACTAAA (SEQ ID NO: 3), shRNA 4 ACTATGAGACTGCTCTATCAG (SEQ ID NO: 4). The CDK5RAP2 expression construct was generated using the Gateway system (Invitrogen) by PCR amplification of CDK5RAP2 from MGC human CDK5RAP2 cDNA (clone ID: 9052276) using the primers with AttB sites: Forward: GGGGACAAGTTTGTACAAAAAAGCAG-GCTTCATGATGGACTTGGTGTTGGAAGA (SEQ ID NO: 5), Reverse: GGGGACCACTTTGTA-CAAGAAAGCTGGGTCAGCTTTATTGGCTGAAAGT-TCTTCTC (SEQ ID NO: 6). CDK5RAP2 was cloned into destination vector pcDNA3.1/nV5-DEST.

Cerebral Organoid Culture Conditions

Human H9 ES (WA09) were obtained from WiCell at passage 26 with verified normal karyotype and contamination-free. iPS cells were obtained from System Biosciences (SC101A-1) verified pluripotent and contamination free. All human PSC lines were regularly checked and confirmed negative for *mycoplasma*. Human embryonic stem (ES) or induced pluripotent stem (iPS) cells were maintained on CF-1 gamma irradiated MEFs according to WiCell protocols. On day 0 of organoid culture, ESCs or iPSCs were dissociated from MEFs by dispase treatment and MEFs were removed by gravity separation of stem cell colonies from MEFs before trypsinization of stem cells to generate single cells. 4500 cells were then plated in each well of an ultra-low binding 96-well plate in hES media with low bFGF (5-fold reduced) and 50 uM ROCK inhibitor.

Embryoid bodies (EBs) were fed every other day for 6 days then transferred to low adhesion 24-well plates in neural induction media containing DMEM/F12, 1:100 N2 supplement (Invitrogen), Glutamax (Invitrogen), MEM-NEAA, and 1 ug/ml Heparin (Sigma). These began forming neuroepithelial tissues, which were fed every other day for 5 days. On Day 11 of the protocol, tissues were transferred to droplets of Matrigel by pipetting into cold Matrigel on a sheet of Parafilm with small 3 mm dimples. These droplets were allowed to gel at 37 C and were subsequently removed from the Parafilm and grown in differentiation media containing a 1:1 mixture of DMEM/F12 and Neurobasal containing 1:200 N2 supplement, 1:100 B27 supplement without vitamin A (Invitrogen), 3.5 ul/L 2-mercaptoethanol, 1:4000 insulin (Sigma), 1:100 Glutamax (Invitrogen), 1:200 MEM-NEAA.

After 4 days of stationary growth, the tissue droplets were transferred to a spinning bioreactor containing differentiation media as above except B27 supplement with vitamin A was used. Since retinoic acid has been shown to be important for neuronal differentiation in vivo, we included it in the final media used to differentiate the cerebral organoids.

Mouse Organoid Culture Conditions

Mouse A9 ES cells were cultured on Mitomycin C growth inactivated MEFs and passaged according to standard protocols (Tremml et al. 2008). For the generation of mouse organoids, the organoid protocol was applied with the following modifications: cells were trypsinized and 2000 stem cells were plated in each well of an ultra-low binding 96-well plate in differentiation medium as described by Eiraku et al. (medium containing 10 uM SB431542 but without Dkk-1). Subsequent steps were followed according to the human organoid method using identical media compositions, with the exception that for mouse tissues faster timing was used according to morphology. EBs were transferred to neural induction medium on day 4, embedded in matrigel droplets on day 6, and on day 9 transferred to the spinning bioreactor.

Organoid Electroporation

Electroporation was performed using a petri dish tissue electrode and electro-square-porator (ECM 830) both from BTX Harvard Apparatus. A total of 3 ul of 2 ug/ul total plasmid (GFP for live imaging, 1.8 ug/ul shRNA+0.2 ug/ul GFP for shRNA experiments) was injected in 4-5 locations within the organoid and electroporation was performed in differentiation media without antibiotics at 5 pulses, 80V, 50 ms duration, 1 sec interval. For rescue experiments, GFP expression plasmid and the CDK5RAP2 construct were coelectroporated at equal concentrations (1 ug/ul each).

Live Imaging in Organoids

Live imaging was performed using a LSM780 confocal laser scanning system (Zeiss) equipped with temperature and $CO_2$ control. For calcium imaging, Fluo-4 direct (Life Technologies) was prepared according to manufacturer and applied 60 min before the start of imaging. Imaging was performed at 494 nm excitation and 516 nm emission, frames taken every 20 sec for 100 frames. Data analysis of calcium imaging was performed using ImageJ (Fiji). Regions of interest (ROIs) were manually selected and mean fluorescence was calculated for each time frame. Change is fluorescence was calculated as follows: $\Delta F/F=(F-F_{basal}))/F_{background}$ where $F_{basal}$ was the lowest mean fluorescence value across imaging while $F_{background}$ was the average mean fluorescence across all frames. Glutamate was added by bath application to media during imaging at a final concentration 100 uM. TTX was added by bath application to media during imaging at a final concentration of 1 uM and imaging was resumed after a 10 min incubation time.

Histology and Immunofluorescence

Tissues were fixed in 4% paraformaldehyde for 20 min at 4° C. followed by washing in PBS 3 times 10 min. Tissues were allowed to sink in 30% sucrose overnight and then embedded in 10%/7.5% gelatin/sucrose and cryosectioning at 20 μm. Tissue sections were stained with hemotoxylin/eosin or used for immunostaining. For immunohistochemistry, section were blocked and permeabilized in 0.25% Triton-X, 4% normal donkey serum in PBS. Sections were then incubated with primary antibodies in 0.1% Triton-X, 4% normal donkey serum at the following dilutions: N-Cadherin (mouse, BD Biosciences 610920, 1:500), Sox2 (rabbit, Chemicon, AB5603, 1:300), Tuj1 (mouse, Covance MMS-435P, 1:750), TUNEL (In Situ Cell Death Detection Kit-Fluorescein, Roche), FoxG1 (rabbit, Abcam ab18259, 1:200), Emx1 (rabbit, Sigma HPA006421, 1:50), Krox20 (rabbit, Covance PRB-236P, 1:100), Pax2 (mouse, Abnova H00005076-M01, 1:200), Lmo4 (goat, Santa Cruz sc-11122, 1:50), Tshz2 (rabbit, Sigma SAB4500379, 1:50), Otx1+2 (rabbit, Abcam ab21990, 1:200), Gbx2 (goat, Santa Cruz sc22230, 1:100), Auts2 (rabbit, Sigma HPA000390, 1:250), Nkx2.1 (rabbit, Epitomics 6594-1, 1:250), Pax6 (mouse monoclonal, DSHB, 1:200), Pax6 (rabbit, Covance PRB-278P, 1:300), Calretinin (mouse, Swant 6B3, 1:100), Nrp2 (goat, RandD systems AF2215, 1:40), Fzd9 (rabbit, Acris SP4153P, 1:200), Prox1 (mouse, Chemicon MAB5654, 1:200), TTR (sheep, AbD Serotec AHP1837, 1:100), Tbr2 (rabbit, Chemicon AB9618, 1:500), Tbr1 (rabbit, Abcam ab31940, 1:300), MAP2 (mouse, 1:300), PH3 (rabbit, Cell Signaling Technology 9706S, 1:300), P-Vimentin (mouse, MBL International D076-35, 1:250), BrdU (preincubation in 2N HCl 20 min 37 C, rat, AbD Serotec OBT0030CX, 1:500), Baf53a (rabbit, Bethyl IHC-00287, 1:250), Baf53b (rabbit, Abcam ab140642, 1:250), Reelin, (mouse, Millipore MAB5366, 1:200), Ctip2 (rat, Abcam ab18465, 1:100), Satb2 (rabbit, Abcam ab34735, 1:100), DCX (goat, Santa Cruz sc-8066, 1:300), Brn2 (goat, Santa Cruz sc-6029, 1:40). Secondary antibodies used were donkey AlexaFluor 488, 568, and 647 conjugates (Invitrogen, 1:500). For sections stained for BrdU, sections were first incubated with 2N HCl at 37° C. for 20 min followed by washing three times in PBS before blocking.

RT-PCR

Total mRNA samples were isolated from whole organoids or hES cells in triplicate using Trizol reagent (Invitrogen). Potential contaminating DNA was removed using DNA-Free (Ambion) and 1 ug RNA was used for cDNA synthesis using Super-Script III (Life Technologies). PCR conditions and number of cycles (25-35 cycles) for each primer pair were empirically determined using hES cDNA or human fetal brain cDNA (Invitrogen). Cycles were run at 94° C. denaturation for 30 sec, 58-62° C. annealing for 45 sec, depending on primer pair, and 72° C. extension for 30 sec. Primer pairs used were as follows: Oct4a For ggagaagctggagcaaaacc (SEQ ID NO: 7), Rev tggctgaataccttcccaaa (SEQ ID NO: 8); Nanog For gatttgtgggcctgaagaaa (SEQ ID NO: 9), Rev ctttgggactggtggaagaa (SEQ ID NO: 10); Sox1 For tatcttctgctccggctgtt (SEQ ID NO: 11), Rev gggtcttccct-tcctcctc (SEQ ID NO: 12); Pax6 For agttcttcgcaacctggcta (SEQ ID NO: 13), Rev attctctcccctccttcct (SEQ ID NO: 14); Actb For aaatctggcaccacaccttc (SEQ ID NO: 15), Rev agaggcgtacagggatagca (SEQ ID NO: 16); BF1 For aggagggcgagaagaagaac (SEQ ID NO: 17), Rev tgaactcgta-gatgccgttg (SEQ ID NO: 18); Six3 For ctatcaacaaccccaacca (SEQ ID NO: 19), Rev agccgtgcttgtcctagaaa (SEQ ID NO: 20); Krox20 For ttgaccagatgaacggagtg (SEQ ID NO: 21), Rev cttgcccatgtaagtgaaggt (SEQ ID NO: 22); Isl1 For gctttgttagggatgggaaa (SEQ ID NO: 23), Rev actcgatgtgatacac-cttgga (SEQ ID NO: 24).

Cell Culture and Western Blot

HEK293T cells were grown in 10% FBS/DMEM and split at 40% into a 6-well dish (BD Falcon) followed by transfection the next day using TurboFect (Thermo Scientific) with 5 ug plasmid DNA. Cells were lysed 2 days later and western blot was performed using rabbit anti-CDK5RAP2 (A300-554A, Bethyl labs, 1:10,000) followed by blotting for mouse anti-alpha tubulin (mouse, Sigma T6199, 1:10,000). Dermal fibroblasts were obtained by skin punch biopsy and were cultured in amnioMAX C-100 complete medium (Invitrogen) and maintained in a 37° C. incubator with 5% $CO_2$ and 3% $O_2$. Cells were lysed in 50 mM Tris-HCl pH 8, 280 mM NaCl, 0.5% $NP_40$, 0.2 mM EDTA, 0.2 mM EGTA, 10% Glycerol supplemented with protease inhibitor tablet (Roche). Protein samples were run on a 3-8% Tris-acetate gel (Invitrogen) followed by immunoblotting using rabbit anti-CDK5RAP2 (A300-554A, Bethyl labs, 1:2,000) and mouse anti-vinculin (V9264, Sigma, 1:2,000). To perform immunofluorescence, patient fibroblasts were fixed in −20° C. methanol for 7 min and then blocked in PBS/1% bovine serum albumin. Cells were then incubated in rabbit anti-CDK5RAP2 (A300-554A, Bethyl labs, 1:2,000) and mouse anti-CPAP (SC-81432, Santa Cruz Biotechnology, 1:100) in blocking solution. Secondary antibodies used were donkey AlexaFluor 488 and 568 conjugates (Invitrogen, 1:500).

Research Subject and Gene Identification

Genomic DNA was extracted from peripheral blood of Patient 3842 and the patient's parents by standard methods. Informed consent was obtained from the family and the study approved by the Multicentre Research Ethics Committee for Scotland (04:MRE00/19). Whole exome capture and sequencing was performed at the Welcome Trust Sanger Institute (WTSI), UK. DNA was sheared to 150 bp lengths by sonication (Covaris, Woburn, Mass., USA) prior to whole exome capture and amplification using the SureSelect Human All Exon 50 Mb kit (Agilent, Santa Clara, Calif.). Fragments were sequenced using the Illumina Hiseq platform. 76 bp paired end sequence reads were aligned to the UCSC genome browser hg19 reference sequence using BWA. Sequence variants were obtained using GenomeAnalysisTK (www.broadinstitute.org/gatk/) and annotated with transcript and protein consequence, polyphen, condel and SIFT scores. Mutations were confirmed by bi-directional sequencing of PCR products using dye terminator chemistry on an ABI 3730 capillary sequencer (Applied Biosystems).

Patient iPSC Reprogramming

Patient skin fibroblasts were reprogrammed using lentiviral delivery of Oct4, Sox2, Klf4, and c-Myc. Lentivirus production: A DNA mix consisting of virus packaging vectors (tat, rev, gag/pol, 1.5 ug each, and vsv-g, 3 ug) and the loxP flanked OKSM reprogramming vector (oct-4, klf4, sox2, c-myc, 30 ug) were transfected into 293 cells. In brief, 112.5 µl Fugene6 was added dropwise to 2 ml DMEM under constant vortexing followed by a 10 min incubation at RT. The DNA mix was added to the DMEM/Fugene6 mix while vortexing to generate the final transfection mix. After a 15 min incubation at RT, the transfection mix was added onto 80% confluent 293 cells, cultured in 13 ml 293 culture medium. Virus-containing medium was harvested and replaced with fresh medium 48 h, 60 h and 72 h after transfection. The viral supernatant was stored at 4° C. Reprogramming of human dermal fibroblasts: $1 \times 10^5$ dermal fibroblasts were seeded the day before infection onto 10 cm and 6 cm 0.1% Gelatin-coated culture dishes. Cells were incubated for 12 h with viral supernatant 1:1 mixed with dermal fibroblast medium supplemented with 4 µg/ml polybrene. Thereafter, cells were washed with 1×PBS and cultured for 2 more days in dermal fibroblast medium. After 2 days medium was switched to human iPSCs medium supplemented with 10 ng/ml bFGF (peprotech, cat.nr: 100-18B), 10 µM CHIR99021 (stemgent, cat.nr: 04-0004) and 1 µM PD 0325901 (stemgent, cat.nr: 04-0006) and cells cultured for 21 days. Medium was changed every day. Outgrowing colonies, identified by morphological appearance, were picked and passaged on inactivated CF-1 MEFs (global stem, cat.nr: GSC-6201M). Patient derived iPS lines were compared to control iPS cells obtained from a healthy donor (System Biosciences, SC101A-1). Alkaline phosphatase staining was performed using Vector Blue Alkaline Phosphatase Substrate Kit (Vector Laboratories, SK5300). Quantifications in patient and control iPSC derived organoids were performed blinded using coded file names in ImageJ.

Patient Clinical Synopsis

Patient A3842 exhibited growth restriction from fetal life, with marked reduction in brain size evident at 22/40 weeks gestation. Pregnancy progressed otherwise normally and the patient was born at term weighing 1.82 kg (−3.9 s.d.). Postnatally, growth was also reduced such that height at 3 years 7 months was 73 cm (−6.7 s.d.), and head circumference 35 cm (−13.2 s.d.), in keeping with a severe disproportionate microcephaly. The patient had quite prominent eyes and conical shaped wide-space teeth, but was otherwise unremarkable on examination. No neurological deficits or malformations in other systems were evident, aside from a mixed conductive/sensorineural hearing loss. Development milestones were mildly/moderately delayed. Neuroimaging at 22/40 gestation demonstrated a smooth brain (the Sylvian fissure normally evident at this gestation was not present) with small frontal lobes and partial absence of the corpus callosum. Postnatally, MRI demonstrated microcephaly with a simplified gyral pattern and a cerebral cortex of normal thickness. In summary, clinical findings were in keeping with previous cases of CDK5RAP2 primary microcephaly (deafness has been previously reported with CDK5RAP2), with growth parameters falling on the primary microcephaly-microcephalic primordial dwarfism spectrum reported for other centrosomal microcephaly genes such as CENPJ and CEP152.

Example 2: The Spinning Droplet Method for Production of Cerebral Organoids

Recent progress with in vitro models of various organ systems has demonstrated the enormous self-organizing capacity for pluripotent stem cells to form whole tissues. In developing an approach to model the complexity and heterogeneity of the human brain, we built upon this concept and left out any patterning growth factors that would artificially drive particular brain regions. We focused instead on improving upon the growth requirements of the tissue and providing the environment necessary for intrinsic cues to influence development rather than driving formation of specific brain regions extrinsically.

We began with a modified approach to generate neuroectoderm from embryoid bodies similar to that used to generate neural rosettes (Xia and Zhang. 2009). However, the key difference in our approach is that these neuroectodermal tissues were then maintained in 3D culture and embedded in droplets of Matrigel, which were then transferred to a spinning bioreactor to enhance nutrient absorption and allow for growth of larger more complex tissues (FIG. 1a).

This spinning droplet approach led to the formation of large, continuous neuroepithelia surrounding a fluid filled cavity reminiscent of a ventricle (FIG. 1b). These neuroepithelia displayed characteristic expression of the neural specific N-cadherin, which localized specifically to the inner surface reflecting apical-basal polarity typical for developing neuroepithelium. Furthermore, the neuroepithelium was larger and more continuous than tissues generated similar to Eiraku et al. (2008), which instead formed an aggregate of several small rosette-like neuroepithelia (FIG. 1b, e).

When these tissues were allowed to continue to develop further, organoids formed very large (up to 4 mm in diameter), highly complex heterogeneous tissues with structural characteristics reminiscent of various brain regions (FIG. 1c-e), which could survive indefinitely (currently up to 10 months) when maintained in a spinning bioreactor. Histological and gross morphological analysis revealed regions reminiscent of cerebral cortex, choroid plexus, retina, and meninges. Importantly, tissues typically reached a size limit likely due to the lack of a circulatory system and limitations in oxygen and nutrient exchange. Consistent with this, extensive cell death was visible in the core of these tissues (FIG. 14c), whereas the various brain regions developed along the exterior. Furthermore, cerebral organoids could be reproducibly generated with similar overall morphology and complexity from both human ES cells and induced pluripotent stem cells (iPSCs) (FIG. 7a, b), suggesting this approach could be applied to a variety of human pluripotent stem cells.

Example 3: Cerebral Organoids Display Various Discrete Brain Regions

Since gross morphological analyses suggested the cerebral organoids displayed heterogeneous brain regions, we next sought to characterize region identity of these tissues. We first performed RT-PCR for several markers of pluripotency and neural identity (FIG. 8) and found that while the pluripotency markers Oct4 and Nanog diminished during the course of organoid differentiation, the neural identity markers Sox1 and Pax6 were upregulated, indicating successful neural induction of these tissues.

We next examined regional markers of neural identity in whole organoids (FIG. 2a), which revealed the presence of both forebrain markers (BF1 and Six3) as well as hindbrain (Krox20 and Isl1) markers suggesting a heterogeneous population within the tissue. However, we noticed that as tissues developed to more advanced stages, forebrain markers remained highly expressed while hindbrain markers began to decrease, suggesting the relative amounts within the tissues of these identities changed over the course of differentiation. This is particularly interesting in light of the fact that normal human brain development reflects a similar change in relative amounts of these identities due to the developmental expansion of forebrain tissue, eventually constituting approximately 85% of the human brain.

We then examined whether cells with these brain region identities developed as discrete regions within the organoids, as gross morphology would suggest, or were randomly interspersed within the tissue. To test this, we performed immunohistochemical staining for markers of forebrain and midbrain as well as hindbrain identities at two time points during the early development of these tissues (FIG. 2b). We could clearly identify several regions of forebrain identity by Pax6 expression and of forebrain/midbrain identity, as determined by Otx1/2 expression. These regions were located adjacent to regions lacking these markers but positive for hindbrain markers Gbx2, Krox20, and Pax2, which was reminiscent of the early mid-hindbrain boundary, suggesting similar regional communication and likely mutual repression. We additionally observed that regions of Gbx2 positivity decreased in abundance as development progressed, similar to results seen in FIG. 2a, whereas Otx1/2 positive forebrain tissues continued to expand.

We next examined further developed tissues to test whether subregions of the forebrain could be distinguished. We performed staining for the forebrain marker FoxG1 (FIG. 2c), which labeled regions displaying typical cerebral cortical morphology. Many of these regions were also positive for Emx1 (FIG. 2d), indicating dorsal cortical identity. We could identify several discrete regions within the cerebral organoids that stained positively for this marker and displayed typical dorsal cortical morphology. We also tested for subspecification within the dorsal cortex, namely the frontal cortex, by staining for the marker Auts2 (FIG. 2d). Auts2 staining could be seen in neurons labeling distinct regions of dorsal cortex, suggesting subspecification of cortical lobes within the tissues. Tshz2, a marker of the occipital lobe (FIG. 15a), and Lmo4, a marker of frontal and occipital lobes but absent in parietal (FIG. 15b). These markers could be seen in neurons labeling distinct regions of dorsal cortex, suggesting subspecification of cortical lobes.

Furthermore, staining for other cerebral cortical regions, namely the ventral cortex (FIG. 2e) and hippocampus (FIG. 2f), similarly revealed discrete regions within organoids that displayed these identities as well. Strikingly, interneurons produced in ventral forebrain regions exhibited a morphology and location consistent with migration from ventral to dorsal tissues (FIG. 15b). Within dorsal cortex, these neurons displayed neurites parallel to the apical surface, reminiscent of the migratory extensions seen in tangential migration in vivo (FIG. 5g). Notably, Calretinin positive interneurons were absent from dorsal cortex of organoids lacking a ventral region (4/4 Nkx2.1 negative organoids), suggesting interneurons originate in ventral forebrain to migrate to the dorsal cortex. This suggests distant regions can influence one another in developing cerebral organoids.

Finally, other brain structures separate from these cerebral cortical identities could be observed, namely choroid plexus (FIG. 2g) and even immature retina (FIG. 10d). Overall, all tissues examined displayed regions with dorsal cortical morphology (35/35, 100%), most displayed choroid plexus (25/35, 71%) and several displayed ventral forebrain identity as determined by Nkx2.1 immunoreactivity (12/35, 34%), whereas only a few displayed retinal tissue (determined by presence of retinal pigmented epithelium, 4/35, 11%). These results suggest that cerebral organoids developed a variety of brain region identities organized into discrete, though interdependent, domains.

Example 4: Dorsal Cortical Organization and Radial Glial Behavior is Recapitulated in Cerebral Organoids Since we were interested in modeling development and disease of the human dorsal cortex, we next examined the organization of dorsal cortical regions within cerebral organoids. Staining for markers of radial glial progenitors (RGs) and newborn neurons (FIG. 3a) revealed typical progenitor zone organization with RGs forming a layer adjacent to a large fluid-filled cavity reminiscent of a ventricle, suggesting the formation of a ventricular zone (VZ). Staining for Tbr1 (FIG. 11a) revealed proper development of neural identity and radial migration to the developing preplate (precursor to CP). Furthermore, staining for neural progenitor and neural specific BAF components revealed the characteristic switch in chromatin remodeling complexes during neural fate specification (FIG. 16a). Furthermore, staining for the intermediate progenitor (IP) marker Tbr2 (FIG. 3b) revealed a thin layer of IPs adjacent to the VZ, which was reminiscent of the subventricular zone (SVZ). Thus, dorsal cortical tissues display typical progenitor zone organization much like that seen in vivo.

We next examined whether the behavior of these progenitors reflected that seen in the mammalian cerebral cortex. We examined proliferation within these tissues by staining for phospho-histone H3 (PH3) (FIG. 3c) and observed the majority of cells dividing at the apical surface, adjacent to the fluid-filled cavity, likely marking the divisions of RGs, which typically divide on the apical surface. We could additionally observe occasional divisions outside the VZ likely reflecting transit-amplifying divisions of IPs and potentially divisions of a recently identified stem cell population, outer radial glia (discussed in more detail below).

Furthermore, when we stained for phospho-Vimentin (FIG. 3d), a marker of mitotic RGs, we could observe the majority of divisions occurring at the apical surface, similar to PH3 staining, but we could also observe clear basal processes extending all the way to the outer surface of these tissues (FIG. 3e). This suggests RGs within these tissues recapitulated the typical apical-basal morphology seen in vivo.

To examine this in more detail, we sought to label individual RGs using an electroporation approach. Drawing from our experience with in utero electroporation in the mouse embryonic brain, we developed a technique to inject plasmid DNA encoding GFP into the fluid filled cavities of these tissues and then apply a square-wave pulse electric field to electroporate RGs adjacent to these ventricle-like cavities (FIG. 3f). This approach led to reproducible expression of GFP within several regions and in cells located adjacent to fluid-filled cavities.

When we examined GFP labeled cells within these dorsal cortical regions, we could identify RGs with typical morphology at various stages of development (FIG. 3g). For example, in earlier stage tissues, RGs displayed neuroepithelial morphology reflecting the pseudostratified structure seen early in development. However, later stage tissues displayed RGs with longer extended apical and basal processes reflecting the bipolar morphology of these cells.

The observation that division of RGs occurred at the apical surface, suggested that RGs may undergo typical interkinetic nuclear migration. To test this, we performed live imaging of GFP electroporated RGs in cerebral organoids. We could observe many examples of RGs that displayed movement of the cell body along the apical and basal processes (FIG. 4a) consistent with interkinetic nuclear migration.

Furthermore, we performed pulse-chase experiments with the S-phase marker BrdU to test whether nuclei of RGs shifted from outer VZ localization towards the apical surface with time, as would be expected if the cells were undergoing interkinetic nuclear migration. Indeed, following a short 1-hour pulse of BrdU, the majority of cells localized to the outer region of the VZ (FIG. 4b). However after washing and a 4-hour or 6-hour chase we could observe progressively more cell nuclei stained positively for BrdU closer to and adjacent to the apical surface. This is consistent with typical RG interkinetic nuclear migration behavior.

We next examined the division mode of RGs at the apical surface. We had already observed that P-Vimentin stained mitotic RGs at the apical surface nicely (FIG. 4c), and we could clearly discern the plane of division from this staining. We therefore performed measurements of the plane of division (FIG. 4d) to examine whether human RGs within these cerebral organoids displayed similar mitotic orientations to those seen in other model systems, namely the developing mouse neocortex. We observed primarily planar orientations, which were parallel to the apical surface (FIG. 4d), which has often been observed in development of other mammalian neocortex. However, we also observed quite abundant oblique orientations, which were present to a larger extent in these human tissues than has typically been described for the developing rodent neocortex. Interestingly, these measurements reflected the same trend recently described in the human brain, suggesting the cerebral organoids could recapitulate aspects of human cortical development.

We further examined the fate potential of these divisions to test whether RGs in human cerebral organoids could divide symmetrically or asymmetrically. We performed electroporation of GFP followed by a short BrdU pulse-chase to lineage trace divisions of a small minority of cells. When we examined double-labeled daughter cell pairs, we could observe both symmetric self-renewing RG fates, as well as asymmetric fates with only one daughter cell remaining an RG (FIG. 4e, f). This suggests the RGs generated in these human tissues could undergo both symmetric and asymmetric divisions.

Example 5: Formation of Functional Cerebral Cortical Neurons

The formation of the radially organized CP begins with the formation of its precursor, the preplate. To test for this initial organization, we stained 30-day organoids for Tbr1, a marker of the preplate, as well as Map2, a neuronal marker38 (FIG. 12a). This revealed the presence of a basal neural layer reminiscent of the preplate, and an apically adjacent region reminiscent of the IZ. Furthermore, we could observe Reelin positive neurons along the basal surface, suggesting the presence of Cajal-Retzius cells, an important population in generation of CP architecture.

In vivo, dorsal cortical neurons mature and extend long-range axons. To test for these characteristics, we performed GFP electroporation and examined neuronal morphology. GFP-labeled axon projections displayed complex branching and growth cone behavior (FIG. 5i) and projected long-range axons in a manner reminiscent of axon bundling (FIG. 5h).

Finally, we tested whether neurons within cerebral organoids could exhibited neural activity by performing calcium dye imaging to detect $Ca^{2+}$ oscillations, which revealed spontaneous calcium surges in individual cells (FIG. 5j, FIG. 17b). Furthermore, we applied exogenous glutamate (FIG. 12c) and observed more frequent calcium spikes, indicating glutamatergic receptor activity. Finally, we performed action potential blockade by application of tetrodotoxin (TTX) and observed dampened calcium surges indicating calcium spikes were dependent upon neuronal activity (FIG. 12d).

Example 6: Recapitulation of Later Events in Human Cerebral Cortical Development In order to examine whether cerebral organoids could be used to study human specific processes in neuronal development, we examined progenitor zone morphology in developmentally more advanced dorsal cortical tissues. These regions were typically much thicker and very large (a single dorsal cortical region within an organoid could grow up to 1 mm across) if allowed to develop to a more advanced stage. We stained for RGs and neurons and observed a large number of Sox2-positive progenitors that appear displaced from the apical surface (FIG. 5a, FIG. 18a). The marker identity and location of these progenitors point to the possibility that they represent outer radial glia (oRGs), a recently identified progenitor type that is highly overrepresented in the human cerebral cortex compared with mice and other lower mammals.

To rule out the possibility that this OSVZ-like organization was an in vitro artifact, we adapted the method to mouse ES cells to generate mouse cerebral organoids and examined whether a similar organization was present (FIGS. 18b and c). We observed much smaller cortical tissues in mouse organoids compared with human, and only occasional oRGs that did not accumulate in an OSVZ-like region. These results suggest OSVZ and IFL-like layers are specific to human organoids.

We furthermore observed that these fairly abundant oRGs appeared separated from the apical VZ by a Tuj1 positive fiber layer (FIG. 5a) reminiscent of the inner fiber layer seen in human but not mouse developing cortex. This organization suggests human cerebral organoids could recapitulate at least some aspects of human-specific cortical development that cannot be modeled in mouse.

In order to further characterize these potential oRGs, we performed P-Vimentin staining to examine their morphology and observed obvious basal processes emanating from these cells, whereas they lacked apical processes (FIG. 5b). This morphology, along with RG marker identity, is a hallmark of oRGs suggesting these basally displaced Sox2 and P-Vimentin positive progenitors indeed represent human oRGs.

We next examined the division mode of these oRGs and could identify asymmetric divisions as labeled by daughter cell pairs with P-Vimentin in which only one daughter cell maintained Sox2 expression (FIG. 5c). Furthermore, we could measure the division plane relative to the apical surface and found that the vast majority of oRGs divided perpendicular to the apical surface (FIG. 5d). These findings suggest that cerebral organoids could be a useful model system to study various aspects of human oRGs.

As a final characterization of the human cerebral organoids, we sought to describe the identity and behavior of the neurons produced in the dorsal cortical regions. We began by staining for cerebral cortical layer markers during advanced stages of development of these tissues. Previous methods of deriving cortical neurons have been able to generate various layer identity neurons, and we were similarly able to generate several layer identities using this approach. However, whereas other methods have notably failed to recapitulate the spatial organization of the neuron layers, our cerebral organoids displayed at least rudimentary separation of layers (FIG. 5e) and this spatial separation became more discrete as tissues were allowed to develop (FIG. 5f).

Furthermore, we observed an organization reminiscent of the inside-out pattern seen in developing mammalian cortex in vivo. Specifically, the later born neurons marked by Brn2 and Satb2 localized more to the outer regions of the tissue while the earlier born neurons marked by Ctip2 remained in the inner region (FIG. 5e, f). This suggests these 3D tissues may better recapitulate neuronal migration events than any previously described in vitro methods of generating cerebral cortical neurons.

Along these lines, we could even observe calretinin positive cortical interneurons within the dorsal cortical plate and exhibiting migratory processes parallel to the apical surface consistent with tangential migration (FIG. 5g). Within other areas of these organoids, we could identify ventral cortical regions exhibiting calretinin positive neurons quite removed from the dorsal cortex. This suggests the calretinin positive interneurons could migrate over a fairly long-range to reach their destination within the dorsal cortex, much like the developing cerebral cortex in vivo.

We next scrutinized the morphology of the dorsal cortical neurons by examining GFP electroporated cells in tissues several days following electroporation. We could identify clusters of maturing cortical pyramidal cells, likely born at approximately the same time, that projected long-range axons together to the same distant location within the organoid (FIG. 5h). Furthermore, pyramidal neuron axon projections displayed complex branching and growth cone behavior (FIG. 5i) similar to that described in vivo.

Finally, we tested whether neurons produced within cerebral organoids displayed neural activity by performing calcium imaging to detect Ca2+ oscillations. Using the calcium sensitive dye Fluo-4, we could detect spontaneous calcium surges in individual neurons (FIG. 5j). These findings suggest cerebral organoid neurons were capable of maturation and synaptic activity.

Example 7: Cerebral Organoids Model Microcephaly and Implicate Premature Neural Differentiation Microcephaly is a neurodevelopmental disorder presenting with small (greater than 2 standard deviations below the mean) head circumference, which stems from the development of a greatly reduced brain size. Several genes have been identified in primary microcephaly as well as several overlapping disorders, such as microcephalic osteodysplastic primordial dwarfism (MOPD) and Seckel syndrome. While evidence in model systems suggests many of the genes identified in these disorders may function at the centrosome or in DNA repair, the human microcephaly phenotype has been notably difficult to model, as mouse mutants often do not display the same severity of phenotype. Since this disorder reflects a defect in brain enlargement during development, and the human brain exhibits important divergences in mechanisms of expansion, we hypothesized that the human cerebral organoids may better model aspects of this disorder.

We identified a patient with severe microcephaly (−13.2 standard deviation below mean for age and sex) (FIG. 6a) and reduced stature (−6.7 s.d.), who, as determined through exome sequencing and confirmed by capillary sequencing (FIG. 6b), had compound heterozygous truncating mutations in the coding sequence of the previously identified primary microcephaly gene CDK5RAP2 (FIG. 6b). Both mutations led to premature stop codons in a similar region of the protein, suggesting this may reflect homozygous null mutation.

We obtained skin fibroblasts from this patient and performed western blot (FIG. 6c) as well as immunocytochemical staining for the Cdk5Rap2 protein (FIG. 6d). We could detect no protein in these patient cells, supporting the hypothesis that the microcephaly is due to the absence of the Cdk5Rap2 protein.

In order to model the phenotype in our organoid system, we next performed reprogramming of these patient skin fibroblasts using lentiviral delivery of the four well-described reprogramming factors: Oct4, Sox2, c-Myc, and Klf4. We were able to generate several independent clones of iPSCs and characterized four of these for morphology and pluripotency. All four lines exhibited similar doubling times as well as colony morphology that were indistinguishable from control human iPSCs (FIG. 9a). All lines could form embryoid bodies and exhibited positive staining for the pluripotency marker alkaline phosphatase (FIG. 9b).

We next performed cerebral organoid culture from all of these 4 lines and could observe that when transferred to neural induction media, EBs failed to develop further compared with control, and instead remained quite small (FIG. 9c). We hypothesized that since the patient also displayed dwarfism, perhaps overall growth was perturbed as well. We therefore modified the protocol slightly by plating double the starting number of iPSCs thereby allowing EBs to develop further before transferring to neural induction. Indeed this approach allowed for the formation of neuroectoderm and subsequent neural tissue. However, gross morphology revealed that all four lines displayed smaller neuroepithelial tissues and a large degree of neuronal outgrowth compared with control tissues (FIG. 6e and FIG. 9d).

In order to examine this further, we allowed the tissues to an advanced stage and examined the overall morphology by immunohistochemical staining for progenitors and neurons (FIG. 6f). We could observe overall smaller neural tissues with only very few regions exhibiting progenitors surrounding very small fluid-filled lumens compared with control. These overall smaller neural tissues were reminiscent of the greatly reduced brain size seen in humans with microcephaly.

We next sought to examine the cause of the hypoplasia seen in these patient cerebral organoids. To this end, we examined earlier stage tissues by immunohistochemistry for progenitors and neurons. Whereas control tissues at this stage displayed an abundance of large fluid-filled tissues primarily composed of progenitors, we could observe only occasional small fluid-filled lumens surrounded by progenitors in the patient derived tissues (FIG. 6g, FIG. 20a). Furthermore, patient tissues exhibited relatively increased neurons compared with control suggesting premature neural differentiation (FIG. 6h), perhaps at the expense of progenitors. To test this possibility, we performed BrdU pulse-chase experiments (FIG. 13b) revealing a dramatic increase in the number of BrdU+/DCX+ cells in patient organoids, consistent with premature neurogenic non-proliferative divisions.

Since these patient tissues lack the Cdk5Rap2 protein even before initiation of neural induction, we next investigated whether an acute loss of the protein after the formation of cerebral organoids would lead to a similar defect. To this end, we performed RNAi mediated knockdown of Cdk5Rap2 by co-electroplating GFP along with three independent shRNAs (shRNA1, shRNA2, shRNA4) found to knockdown endogenous Cdk5Rap2 in human 293T cells (FIG. 9e). All three shRNAs gave similar results, namely a striking loss of Sox2+ progenitors in the zone of electroporation and an increase in DCX+ newborn neurons (FIG. 6i). Of note, shRNA4 gave a weaker phenotype likely because this shRNA did not exhibit the same efficiency of knockdown.

Finally, we tested whether the phenotype could be rescued by reintroducing CDK5RAP2 protein. We performed coelectroporation of GFP and CDK5RAP2 into day 12 patient organoids and examined 6 days later. Since high overexpression of CDK5RAP2 was toxic (data not shown), the cells with high GFP signal did not survive to this time point. However, we could observe regions in CDK5RAP2 electroporated tissues with larger neuroepithelium compared with tissues electroporated only with GFP (Extended Data FIG. 20b). This effect could be due to surviving cells with a low-level of CDK5RAP2 re-expression. Supporting this interpretation, staining for GFP (FIG. 20c) revealed many low-level GFP+ cells in CDK5RAP2 coelectroporated patient organoids with radial glial morphology (54%+/−2 SEM, n=74 cells from 3 tissues). In contrast, GFP+ cells in patient organoids electroporated with GFP alone exhibited mainly neuronal morphology with significantly fewer radial glia (19%+/−11 SEM, n=102 cells from 3 tissues, P<0.05, Student's t-test). Thus, we conclude that the phenotype is specific to loss of CDK5RAP2.

When we examined this phenotype in more detail, we could observe that virtually all of the GFP shRNA co-electroporated cells exhibited neural morphology and costaining for DCX (FIG. 6j). These findings suggest that, similar to patient derived tissues, acute knockdown of Cdk5Rap2 leads to premature neural differentiation at the expense of progenitors. This could lead to the overall size decrease seen in patient derived tissues as well as patients with microcephaly since a loss of progenitors would be expected to lead to a final decrease in overall tissue growth.

As a further independent approach, we performed RNAi knockdown of CDK5RAP2 by co-electroplating GFP with two independent shRNAs found to knockdown endogenous CDK5RAP2 (FIG. 21a). Both shRNAs led to a striking loss of $Sox2^+$ progenitors and an increase in $DCX^+$ neurons (FIG. 6j, FIG. 21b) reflecting a statistically significant increase in neuron production rather than progenitor maintenance (FIG. 21b). These findings support the conclusion that loss of CDK5RAP2 leads to premature neural differentiation at the expense of progenitors.

Example 8: Recapitulation

Human brain development exhibits a number of unique characteristics that we are only beginning to tease out. Most of what we know about human brain development has been limited to fundamental processes shared with rodents and other lower mammals. While these insights have been indispensible in understanding basic mechanisms of brain development, these neurodevelopmental studies have been limited by the model systems available.

We have established a novel approach to studying human neurodevelopmental processes through in vitro culture of cerebral organoids from human pluripotent stem cells. This method recapitulates not only these basic mechanisms of neurodevelopment shared with mice and rats, but also displays many characteristics of human brain development. We are hopeful that this method will allow the study of a variety of human specific neurodevelopmental processes.

Furthermore, a primary goal in neuroscience is to understand the roots of human neurological disease. We have modeled at least some aspects of the human neurodevelopmental disorder microcephaly in these cerebral organoids. The finding that progenitor zones in patient derived tissues display premature neural differentiation at the expense of early progenitors supports a model in which the founder population of radial glial progenitors fails to properly expand in patient tissues, thereby leading to an overall smaller brain.

This may also explain why mouse models have been unable to recapitulate the severity of the disorder in humans. It is hypothesized that the mouse founder population of neural progenitors do not undergo expansion to the same extent as in human before the onset of neurogenesis. Thus, a disruption of this expansion in the founder population in mice would not lead to as severe of an effect as that seen in humans. Overall, our findings suggest we can utilize this in vitro culture system to model aspects of human neurodevelopment and neurological disease and hopefully provide novel insight into the root causes of these disorders.

REFERENCES

Barrera et al. Dev Cell (2010) 18 (6): 913-26
Bond et al. Nat Genet (2002) 32 (2): 316-20
Bond et al. Nat Genet (2005) 37 (4): 353-5
Cox et al. Trends Mol Med (2006) 12 (8): 358-66
Eiraku et al. Cell Stem Cell (2008) 3: 519-532
Elkabetz et al. Genes Dev (2008) 22 (2): 152-65
Fietz et al. Nat Neurosci (2010) 13 (6): 690-9
Fietz and Huttner. Curr Opin Neurobiol (2011) 21 (1): 23-35
Götz and Huttner. Nat Rev Mol Cell Biol (2005) 6 (10): 777-88
Hansen et al. Nature (2010) 464 (7288): 554-561
Kenny et al. Mol Oncol (2007) 1 (1): 84-96
Koch et al. Proc Natl Acad Sci USA (2009) 106 (9): 3225-30
Lizarraga et al. Development (2010) 137 (11): 1907-17
Lui et al. Cell (2011) 146 (1): 18-36
Megraw et al. Trends Cell Biol (2011) 21 (8): 470-80
Price and Brewer. Protocols for Neural Cell Culture: Third Edition. (2001): 255-64
Pulvers et al. Proc Natl Acad Sci USA (2010) 107 (38): 16595-600
Reynolds and Weiss. Science (1992) 255 (5052): 1707-10
Sato et al. Nature (2009) 459 (7244): 262-5
Shi et al. Nat Neurosci (2012) 15 (3): 477-86, S1
Thornton and Woods. Trends Genet (2009) 25 (11): 501-10
Tremml et al. *Curr Protoc Stem Cell Biol* Chapter 1, Unit 1C.4 (2008)
Wang et al., Nature Neuroscience, 14 (5) (2011): 555-561
Wilson and Stice. Stem Cell Rev (2006) 2 (1): 67-77
Xia and Zhang. Methods Mol Biol (2009) 549: 51-8
Zhang et al. Nat Biotechnol (2001) 19 (12): 1129-33

These references are incorporated herein by reference. No mentioning of references shall be construed as an acknowledgement of prior art.

The invention claimed is:

1. A three-dimensional neuronal tissue culture comprising outer radial glia cells; and said culture comprises a three dimensional matrix, wherein said three-dimensional matrix is a hydrogel.

2. The tissue culture according to claim 1, wherein said tissue culture forms at least two layers.

3. The tissue culture according to claim 1, wherein said tissue develops apical and dorsal tissue sections.

4. The tissue culture according to claim 1, wherein said tissue is cerebral tissue.

5. The tissue culture according to claim 1, wherein cells of said culture express one or more gene expression markers selected from forebrain markers BF1 and Six3, hindbrain markers Krox20 and Ils1.

6. The tissue culture according to claim 1, wherein forebrain markers are expressed in increased amounts as compared to hindbrain markers in the tissue culture.

7. The tissue culture according to claim 1, wherein cells of said culture express one or more gene expression markers selected from Otx1, Otx2, FoxG1, Auts2, Tuj1, Brn2, Satb2, Ctip2, calretinin.

8. The tissue culture according to claim 1, wherein the three dimensional matrix comprises a collagen.

9. The tissue culture according to claim 1, wherein said outer radial glia cells are in an outer or extra cortical subventricular zone and the tissue further comprises cells of a cortical inner fiber layer in an inner fiber layer.

10. A method of testing a candidate drug for neurological effects, comprising administering a candidate drug to an artificial culture according to claim 1 and determining an activity of interest of the cells of said culture and comparing said activity to an activity of cells to the culture without administering said candidate drug, wherein a differential activity indicates a neurological effect.

11. A method of obtaining a differentiated neural cell, the method comprising the step of providing an artificial culture according to claim 1 and isolating a differentiated neural cell of interest.

12. A method of generating a tissue culture according to claim 1 comprising:
   a) providing a multicellular aggregation of pluripotent stem cells,
   b) culturing said multicellular aggregation in neural induction medium thereby inducing the multicellular aggregation to differentiate to neuroepithelial cells,
   c) culturing said differentiated neuroepithelial cells in drops of extracellular matrix derived from Engelbreth-Holm-Swarm sarcoma cells, thereby expanding said cells in a multicellular aggregation, and
   d) culturing said expanded multicellular aggregation of cells from step c) in a suspension culture, thereby generating the tissue culture according to claim 1.

13. The method of claim 12, wherein said pluripotent cell is an induced pluripotent cell.

14. The method of claim 13, wherein the induced pluripotent cell comprises a cell that has been isolated from a patient.

15. The method of claim 12, further comprising decreasing or increasing the expression in a gene of interest in a cell at any stage during said method, wherein the method is used for investigating a developmental neurological tissue effect.

16. The method of claim 12, further comprising administering a candidate agent to said cells at any stage during the method, wherein the method is used for screening a candidate therapeutic agent suitable for treating a developmental neurological tissue defect of interest.

17. The method of claim 16, wherein administering a candidate agent to said cells at any stage during the method occurs at all stages during the method.

18. A method of obtaining a differentiated neural cell, the method comprising the step of generating an artificial tissue culture according to claim 12 and isolating a differentiated neural cell of interest.

* * * * *

SEQUENCE LISTING

```
<160> NUMBER OF SEQ ID NOS: 24

<210> SEQ ID NO 1
<211> LENGTH: 21
<212> TYPE: DNA
<213> ORGANISM: Artificial
<220> FEATURE:
<223> OTHER INFORMATION: primer

<400> SEQUENCE: 1
aggacgtgtt gcttcagaaa t                                             21

<210> SEQ ID NO 2
<211> LENGTH: 21
<212> TYPE: DNA
<213> ORGANISM: Artificial
<220> FEATURE:
<223> OTHER INFORMATION: primer

<400> SEQUENCE: 2
agagtcagcc ttctgctaaa g                                             21

<210> SEQ ID NO 3
<211> LENGTH: 21
<212> TYPE: DNA
<213> ORGANISM: Artificial
<220> FEATURE:
<223> OTHER INFORMATION: primer

<400> SEQUENCE: 3
```

```
gtggaagatc tcctaactaa a                                        21

<210> SEQ ID NO 4
<211> LENGTH: 21
<212> TYPE: DNA
<213> ORGANISM: Artificial
<220> FEATURE:
<223> OTHER INFORMATION: primer

<400> SEQUENCE: 4
actatgagac tgctctatca g                                        21

<210> SEQ ID NO 5
<211> LENGTH: 54
<212> TYPE: DNA
<213> ORGANISM: Artificial
<220> FEATURE:
<223> OTHER INFORMATION: primer

<400> SEQUENCE: 5
ggggacaagt ttgtacaaaa aagcaggctt catgatggac ttggtgttgg aaga    54

<210> SEQ ID NO 6
<211> LENGTH: 56
<212> TYPE: DNA
<213> ORGANISM: Artificial
<220> FEATURE:
<223> OTHER INFORMATION: primer

<400> SEQUENCE: 6
ggggaccact ttgtacaaga aagctgggtc agctttattg gctgaaagtt cttctc  56

<210> SEQ ID NO 7
<211> LENGTH: 20
<212> TYPE: DNA
<213> ORGANISM: Artificial
<220> FEATURE:
<223> OTHER INFORMATION: primer

<400> SEQUENCE: 7
ggagaagctg gagcaaaacc                                          20

<210> SEQ ID NO 8
<211> LENGTH: 20
<212> TYPE: DNA
<213> ORGANISM: Artificial
<220> FEATURE:
<223> OTHER INFORMATION: primer

<400> SEQUENCE: 8
tggctgaata ccttcccaaa                                          20

<210> SEQ ID NO 9
<211> LENGTH: 20
<212> TYPE: DNA
<213> ORGANISM: Artificial
<220> FEATURE:
<223> OTHER INFORMATION: primer

<400> SEQUENCE: 9
gatttgtggg cctgaagaaa                                          20

<210> SEQ ID NO 10
<211> LENGTH: 20
<212> TYPE: DNA
```

```
<213> ORGANISM: Artificial
<220> FEATURE:
<223> OTHER INFORMATION: primer

<400> SEQUENCE: 10
ctttgggact ggtggaagaa                                         20

<210> SEQ ID NO 11
<211> LENGTH: 20
<212> TYPE: DNA
<213> ORGANISM: Artificial
<220> FEATURE:
<223> OTHER INFORMATION: primer

<400> SEQUENCE: 11
tatcttctgc tccggctgtt                                         20

<210> SEQ ID NO 12
<211> LENGTH: 19
<212> TYPE: DNA
<213> ORGANISM: Artificial
<220> FEATURE:
<223> OTHER INFORMATION: primer

<400> SEQUENCE: 12
gggtcttccc ttcctcctc                                          19

<210> SEQ ID NO 13
<211> LENGTH: 20
<212> TYPE: DNA
<213> ORGANISM: Artificial
<220> FEATURE:
<223> OTHER INFORMATION: primer

<400> SEQUENCE: 13
agttcttcgc aacctggcta                                         20

<210> SEQ ID NO 14
<211> LENGTH: 20
<212> TYPE: DNA
<213> ORGANISM: Artificial
<220> FEATURE:
<223> OTHER INFORMATION: primer

<400> SEQUENCE: 14
attctctccc cctccttcct                                         20

<210> SEQ ID NO 15
<211> LENGTH: 20
<212> TYPE: DNA
<213> ORGANISM: Artificial
<220> FEATURE:
<223> OTHER INFORMATION: primer

<400> SEQUENCE: 15
aaatctggca ccacaccttc                                         20

<210> SEQ ID NO 16
<211> LENGTH: 20
<212> TYPE: DNA
<213> ORGANISM: Artificial
<220> FEATURE:
<223> OTHER INFORMATION: primer

<400> SEQUENCE: 16
agaggcgtac agggatagca                                         20
```

```
<210> SEQ ID NO 17
<211> LENGTH: 20
<212> TYPE: DNA
<213> ORGANISM: Artificial
<220> FEATURE:
<223> OTHER INFORMATION: primer

<400> SEQUENCE: 17
aggagggcga gaagaagaac                                                 20

<210> SEQ ID NO 18
<211> LENGTH: 20
<212> TYPE: DNA
<213> ORGANISM: Artificial
<220> FEATURE:
<223> OTHER INFORMATION: primer

<400> SEQUENCE: 18
tgaactcgta gatgccgttg                                                 20

<210> SEQ ID NO 19
<211> LENGTH: 20
<212> TYPE: DNA
<213> ORGANISM: Artificial
<220> FEATURE:
<223> OTHER INFORMATION: primer

<400> SEQUENCE: 19
ctatcaacaa cccccaacca                                                 20

<210> SEQ ID NO 20
<211> LENGTH: 20
<212> TYPE: DNA
<213> ORGANISM: Artificial
<220> FEATURE:
<223> OTHER INFORMATION: primer

<400> SEQUENCE: 20
agccgtgctt gtcctagaaa                                                 20

<210> SEQ ID NO 21
<211> LENGTH: 20
<212> TYPE: DNA
<213> ORGANISM: Artificial
<220> FEATURE:
<223> OTHER INFORMATION: primer

<400> SEQUENCE: 21
ttgaccagat gaacggagtg                                                 20

<210> SEQ ID NO 22
<211> LENGTH: 21
<212> TYPE: DNA
<213> ORGANISM: Artificial
<220> FEATURE:
<223> OTHER INFORMATION: primer

<400> SEQUENCE: 22
cttgcccatg taagtgaagg t                                               21

<210> SEQ ID NO 23
<211> LENGTH: 20
<212> TYPE: DNA
<213> ORGANISM: Artificial
<220> FEATURE:
```

```
<223> OTHER INFORMATION: primer

<400> SEQUENCE: 23
gctttgttag ggatgggaaa                                              20

<210> SEQ ID NO 24
<211> LENGTH: 22
<212> TYPE: DNA
<213> ORGANISM: Artificial
<220> FEATURE:
<223> OTHER INFORMATION: primer

<400> SEQUENCE: 24
actcgatgtg atacaccttg ga                                           22
```